(12) United States Patent
Bischoff et al.

(10) Patent No.: US 10,544,085 B2
(45) Date of Patent: Jan. 28, 2020

(54) OILS HAVING ANTIBACTERIAL ACTIVITY

(71) Applicant: The United States of America, as Represented by the Secretary of Agriculture, Washington, DC (US)

(72) Inventors: Kenneth M. Bischoff, Morton, IL (US); Timothy D. Leathers, Dunlap, IL (US); Neil P. Price, Edelstein, IL (US); Pennapa Manitchotpisit, Dunlap, IL (US)

(73) Assignee: The United States of America, as Represented by the Secretary of Agriculture, Washington, DC (US)

( * ) Notice: Subject to any disclaimer, the term of this patent is extended or adjusted under 35 U.S.C. 154(b) by 0 days.

(21) Appl. No.: 15/919,395

(22) Filed: Mar. 13, 2018

(65) Prior Publication Data

US 2018/0201571 A1    Jul. 19, 2018

Related U.S. Application Data

(62) Division of application No. 15/126,182, filed as application No. PCT/US2015/020762 on Mar. 16, 2015, now Pat. No. 9,950,986.

(60) Provisional application No. 61/968,094, filed on Mar. 20, 2014.

(51) Int. Cl.
*C07C 69/675* (2006.01)
*A01N 37/36* (2006.01)
(Continued)

(52) U.S. Cl.
CPC ............ *C07C 69/675* (2013.01); *A01N 37/36* (2013.01); *A61K 31/191* (2013.01);
(Continued)

(58) Field of Classification Search
CPC ....... C07C 69/675; C07C 69/21; C07C 69/33; C07C 69/003; A01N 37/36; A61K 31/191
See application file for complete search history.

(56) References Cited

U.S. PATENT DOCUMENTS 8,642,793 B1    2/2014    Kim et al.
8,642,794 B1    2/2014    Kim et al.

OTHER PUBLICATIONS

Patterson, M. J., *Streptococcus*, 1992, Medical Microbiology, 4th Editin, Chapter 13, Galveston (TX): University of Texas Medical Brach at Galveston, NCBI Bookshelf. 25 pages. (Year: 1996).*

(Continued)

*Primary Examiner* — Yate' K Cutliff
(74) *Attorney, Agent, or Firm* — John D. Fado; Maria Restrepo-Hartwig

(57) ABSTRACT

Compounds, called liamocins from *Aureobasidium pullulans*, having the general structure in Formula 1 are disclosed.

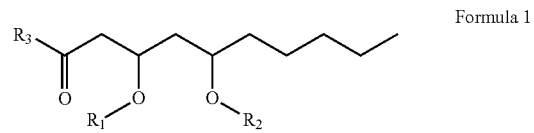

Formula 1 where $R_1$ is either $COCH_3$ or H; and $R_2$ is between two to ten O-linked 3,5-dihydroxydecanoate; and $R_3$ can be a polyol (e.g., L- or D-glycerol, L- or D-threitol, L- or D-erythritol, L- or D-arabitol, L- or D-xylitol, L- or D-lyxitol, L- or D-ribitol, L- or D-allitol, L- or D-altritol, L- or D-mannitol, L- or D-iditol, L- or D-gulitol, L- or D-glucitol (also called sorbitol), L- or D-galactitol (also called dulcitol), and L- or D-talitol), 2-amino-D-mannitol, 2N-acetylamino-D-mannitol, L-rhamnitol, or D-fucitol; except when $R_3$ is D-mannitol, $R_2$ is not 2 nor 3 O-linked 3,5-dihydroxydecanoate (Continued)

Formula 42; 3-O-acetyl-D-mannitol liamocin trimer (D-mannitol liamocin A2)

chains. These liamocins described above in addition to D-mannitol liamocin A1, D-mannitol liamocin A2, D-mannitol liamocin B1, and D-mannitol liamocin B2, alone or in combination with each other, can be used to kill certain bacteria and to treat certain bacterial infections.

4 Claims, 7 Drawing Sheets

(51) Int. Cl.
| | |
|---|---|
| *A61K 31/191* | (2006.01) |
| *C07C 69/21* | (2006.01) |
| *C07C 69/33* | (2006.01) |
| *C07C 69/003* | (2006.01) |
| *C12P 19/44* | (2006.01) |
| *C12P 7/62* | (2006.01) |
| *C12R 1/645* | (2006.01) |

(52) U.S. Cl.
CPC ............ *C07C 69/003* (2013.01); *C07C 69/21* (2013.01); *C07C 69/33* (2013.01); *C12P 7/62* (2013.01); *C12P 19/44* (2013.01); *C12R 1/645* (2013.01)

(56) References Cited

OTHER PUBLICATIONS

Bischoff, Kenneth M. et al., "Liamocin oil from Aureobasidium pullulans has antibacterial activity with specificity for species of *Streptococcus*", (2015) Journal of Antibiotics, advance online publication, Apr. 15, 2015; www.Nature.com, 4 pages.

Manitchotpisit, Pennapa et al., "Aureobasidium pullulans as a source of liamocins (heavy oils) with anticancer activity", (2014) World J Microbiol Biotechnol 30:2199-2204.

Doshida, Junko et al., "Exophilin A, a New Antibiotic from a Marine Microorganism Exophiala pisciphila", (1996) The Journal of Antibiotics 49(11):1105-1109.

Chen, Choryu et al., "Halymecins, New Antimicroalgal Substances Produced by Fungi Isolated from Marine Algae", (1996), The Journal of Antibiotics 49(10):998-1005.

Price, Neil P.J. et al. "Structural characterization of novel extracellular liamocins (mannitol oils) produced by Aureobasidium pullulans strain NRRL 50380", Carbohydrate Research, vol. 370, pp. 24-32, 2013.

Manitchotpisit, Pennapa et al. "Heavy oils produced by Aureobasidium pullulans", Biotechnol Lett, vol. 33, pp. 1151-1157, 2011.

Kurosawa, Takafumi et al. "Extracellular Accumulation of the Polyo Lipids, 3,5-Dihydroxydecanoyl and 5-Hydroxy-2 diecenoyl Esters of Arabitol and Mannitol, by *Aureobasidium* sp.", Biosci. Biotech. Biochem., vol. 58(11), pp. 2057-2060, 1994.

Fisher, K. et al., The ecology, epidemiology and virulence of Enterococcus, 2009, Microbiology, 155, pp. 1749-1757.

Kitamoto, D. et al., Functions and potential applications of glycolipid biosurfactants—from Energy-Saving materials to gene delivery carriers-, 2002, vol. 94, No. 3, pp. 187-201.

Whitman, W. B., et al., Prokarotes: The unsceen majority, 1998, Proc. Natl. Acad. Sci. USA, vol. 95, pp. 6578-6583.

Woese, C.R., et al., Phylogenetic structure of the prokaryotic domain: The primary kingdoms, 1977, Pro. Natl. Acad. Sci. USA, vol. 74, No. 11, pp. 5088-5090.

* cited by examiner

Formula 41; D-mannitol liamocin trimer (D-mannitol liamocin A1)

Formula 42; 3-O-acetyl-D-mannitol liamocin trimer (D-mannitol liamocin A2)

Formula 43, D-mannitol liamocin tetramer (D-mannitol liamocin B1)

Formula 44; 3-O-acetyl-D-mannitol liamocin tetramer (D-mannitol liamocin B2)

OILS HAVING ANTIBACTERIAL ACTIVITY

CROSS-REFERENCE TO RELATED APPLICATIONS

This application is a divisional patent application of U.S. patent application Ser. No. 15/126,182 (allowed) filed on Sep. 14, 2016 which is a National Phase application filed under 35 U.S.C. § 371 as a national stage of PCT/US2015/020762, filed Mar. 16, 2015, which claims priority to U.S. Patent Application 61/968,094 filed Mar. 20, 2014, the contents of each of which are hereby incorporated by reference in its entirety.

BACKGROUND OF INVENTION

Field of Invention

This invention relates to novel oil and its components produced by *Aureobasidium pullulans* and compositions containing these novel oils and its components. These components are liamocins. The liamocin-containing oil and the individual liamocins possess anti-bacterial activity. The liamocins and compositions containing liamocins are used as a topical disinfectant, a transdermal anti-bacterial agent, and a systemically administered antibacterial agent, to name a few. Thus, methods of using the liamocins and compositions containing liamocins to kill bacteria are included in this invention. This invention also relates to methods to produce liamocins with specific head groups.

Discussion of the Prior Art

*Aureobasidium pullulans* is a polymorphic fungus considered to be a filamentous ascomycete in class Dothideomycetes, subclass Dothideomycetidae (Schoch, et al., *Mycologia* 98:1042-1053 (2007); Hibbett, et al., *Mycol. Res.* 111:509-547 (2007)). *A. pullulans* is well-known as the source of the exopolysaccharide pullulan (Leathers, Pullulan. In: Vandamme, et al., (eds.) *Biopolymers, Vol. 6, Polysaccharides II: polysaccharides from eukaryotes*, Wiley-VCH, Weinheim, pp. 1-35 (2002); Singh, et al., *Carbohydr. Polym.* 73:515-531 (2008)). Strains of *A. pullulans* produce numerous other useful bioproducts, including industrial enzymes such as xylanase (Leathers, *J. Ind. Microbiol.* 4:341-348 (1989)). Nagata, et al. (*Biosci. Biotechnol. Biochem.* 57:638-642 (1993)) identified *Aureobasidium* spp. strains that produced poly(β-L-malic acid) (PMA) from glucose. They observed that these cultures also produced extracellular heavier-than-water "oils" (Nagata, et al. (1993)). A partial structure suggested the oils were 3,5-dihydroxydecanoyl and 5-hydroxy-2-decenoyl esters of arabitol and mannitol (Kurosawa, et al., *Biosci. Biotech. Biochem.* 58:2057-2060 (1994)). Oils from these strains were also observed to exert an antiproliferative effect on cancer cell lines (Isoda and Nakahara, *J. Ferment. Bioengin.* 84:403-406 (1997)).

An analysis of the oil revealed a set of novel compounds named liamocins (Price, et al. *Carbohyd. Res.* 370:24-32 (2013)). Four types of liamocins (A1, A2, B1, and B2) were previously identified by Price, et al. (2013). The previously disclosed liamocin A1 and B1 have a single D-mannitol headgroup attached to three or four 3,5-dihydroxydecanoic esters, respectively. The previously disclosed liamocin A2 and B2 are similar in that they have a single mannitol headgroup attached to three or four 3,5-dihydroxydecanoic esters, respectively, but the first dihydroxydecanoic ester, which is attached directly to the mannitol headgroup is 3'-O-acetylated. See FIGS. 1A, 1B, 1C, and 1D for the structures of mannitol-liamocin A1, mannitol-liamocin A2, mannitol-liamocin B1, and mannitol-liamocin B2.

Exophilin A is structurally similar to liamocin. Exophilin A is produced by the marine microorganism *Exophiala pisciphila* and has antimicrobial activity against certain Gram-positive bacteria (Doshida, et al., *J. of Antibiotics* 49(11):1105-1109 (1996)). Doshida, et al. (1996) reported that exophilin A was most active against *Enterococcus faecium* and *E. faecalis* (MICs of 12.5 and 25 µg/ml, respectively) and against three strains of *Staphylococcus aureus* (MIC of 50 µg/ml), but did not inhibit growth of *Streptococcus epidermis* (MIC>100 µg/ml). Of note, *E. pisciphila* strain NBRC 108784, subject of Doshida, et al. (1996) has been reclassified as *A. pullulans* by the National Institute of Technology and Evaluation (NITE) Biological Resource Center (NBRC) in Japan.

*Streptococcus* is a genus of ubiquitous Gram-positive bacteria with both pathogenic and nonpathogenic species. Some species are commensal members of the normal flora of the skin, intestine, and respiratory tracts of animals and humans. Others are recognized as etiologic agents of a number of diseases in veterinary and human medicine. *S. agalactiae* is the most common and recognized species of streptococci that causes mastitis in dairy cattle (Keefe, *Can. Vet. J.* 38(7):429-37 (1997)) and disease in certain fish and other agriculturally important animals. Although less common, *S. uberis* can also cause mastitis problems, spreading to cows from the environment or between cows during milking (Leigh, *The Veterinary Journal* 157(3):225-238 (1999)). *S. suis* is an emerging zoonotic pathogen associated with diseases like septicemia, pneumonia, and endocarditis in pigs (Lun, et al., *The Lancet Infectious Diseases* 7(3): 201-209 (2007)). In human medicine, infections by species of *Streptococcus* cause numerous diseases including, but not limited to, pharyngitis (strep throat), impetigo, sepsis, toxic shock, and necrotizing fasciitis (Cleary, et al., *Medically important beta-hemolytic streptococci*. $3^{rd}$ ed. in: *The Prokaryotes*, (Ed.) M. Dworkin, Vol. 4, Springer. N.Y., pp. 108-148 (2006)).

Mastitis refers to inflammation of the mammary gland. Physical, chemical and usually bacteriological changes in the milk and pathological changes in the glandular tissue characterize it. These glandular changes often result in a number of symptomatic conditions such as, discoloration of the milk, the presence of clots, and the presence of large numbers of leukocytes. Clinically, mastitis is seen as swelling, heat, pain and induration in the mammary gland often resulting in deformation of the udder. In many cases the diagnosis of subclinical infections has come to depend largely on indirect tests which depend on the leukocyte content of the milk or somatic cell count (SCC). Mastitis can occur when the animal's teat and/or udder has been infected by any of several species of bacteria. *Streptococcus* spp., in general, and *S. agalactiae, S. uberis, S. bovis*, and *S. dysgalactiae*, in particular, are a major cause of mastitis. *Enterococcus faecalis* can also cause mastitis.

In a dairy herd, 50% of the intra-mammary infections develop during the nonlactating period of the lactation cycle known as the dry period. The standard management practice to reduce the number of infections during the non-lactating period is to administer systemically a long-lasting and concentrated antibiotic preparation immediately after the last milking preceding the dry period. While this procedure has been effective, it is undesirable from a food safety standpoint. Because of human error, milk tainted with the antibiotic occasionally becomes commingled with milk intended for the market; and, subsequently, the milk must be discarded causing significant economic loss to the dairy producer. In addition, the widespread use of systemic antibiotics is undesirable from the standpoint of creating a population of microorganisms in cattle which may be resistant to antibiotics typically used to treat cattle disease.

Dairy cows are milked for about 305 days and go into a period of non-lactation (dry period) for about 60 days. During the first several days of the dry-period, the mammary gland is very susceptible to infection because the white blood cell count in milk is very low (McDonald and Anderson, *Am. J. Vet. Res.* 42:1366-1368 (1980)). If the gland should become infected, the heifer lacks a sufficiently active immune system within the udder, teats, and mammary glands to keep the bacteria from growing and ultimately resulting in an intramammary infection. It takes about 4-6 days from dry-off for the white blood cells in milk to reach levels that are protective.

In addition to mastitis, *Streptococcus* spp. are involved in many diseases in many different animals. For example, while rumen acidosis may not be initially caused by *S. bovis*, explosive *S. bovis* growth within the rumen occurs during rumen acidosis, resulting in the rumen's pH dropping even further. Several species of *Streptococcus* are known pathogens for marine and freshwater fish, including, but not limited to, *S. difficilis, S. milleri, S. parauberis, S. agalactiae*, and *S. iniae*. *S. pneumoniae* causes pneumonia in animals and humans. *S. agalactiae* causes septicemia in humans and farm animals. *S. pyogenes* causes strep throat, necrotizing fasciitis, and other diseases in humans, while *S. mutans* causes dental caries.

There is a need for a new method of preventing or treating infections by *Streptococcus* spp., in general, and specific species of *Streptococcus*. There is also a need for chemicals and compositions that can kill *Streptococcus* spp., in general, and specific species of *Streptococcus*, when applied to a surface containing the bacteria.

BRIEF DESCRIPTION OF THE INVENTION

It is an object of this invention to have an isolated and novel compound that is an oil and has the structure in Formula 1

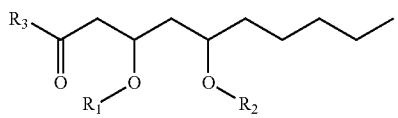

Formula 1 where $R_1$ is, independently, either $COCH_3$ or H; and $R_2$ is, independently, between two to ten O-linked 3,5-dihydroxydecanoate; and $R_3$ is, independently, one of the following: L- or D-glycerol, L- or D-threitol, L- or D-erythritol, L- or D-arabitol, L- or D-xylitol, L- or D-lyxitol, L- or D-ribitol, L- or D-allitol, L- or D-altritol, L- or D-mannitol, L- or D-iditol, L- or D-gulitol, L- or D-glucitol, L- or D-galactitol, L- or D-talitol, 2-amino-D-mannitol, 2N-acetylamino-D-mannitol, L-rhamnitol, or D-fucitol; except when $R_3$ is D-mannitol, $R_2$ is not 2 nor 3 O-linked 3,5-dihydroxydecanoate chains. It is a further object of this invention to have a composition containing one or more of these isolated and purified compounds, optionally a carrier, and optionally a diluent, such that the isolated and purified compounds can kill bacteria, and, more particularly, *Streptococcus* spp., *Enterococcus* spp., and *Bacillus* spp.

It is another object of this invention to have a method of treating a disease caused by a bacterial infection in an animal having said disease by administering a therapeutically effective amount of a composition to the animal having the disease, the amount being effective to kill the bacteria causing the disease, and the composition contains an oil having the chemical structure of Formula 1

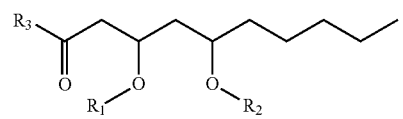

Formula 1 where $R_1$ is, independently, either $COCH_3$ or H; and $R_2$ is, independently, between two to ten O-linked 3,5-dihydroxydecanoate; and $R_3$ is, independently, one of the following: L- or D-glycerol, L- or D-threitol, L- or D-erythritol, L- or D-arabitol, L- or D-xylitol, L- or D-lyxitol, L- or D-ribitol, L- or D-allitol, L- or D-altritol, L- or D-mannitol, L- or D-iditol, L- or D-gulitol, L- or D-glucitol, L- or D-galactitol, L- or D-talitol, 2-amino-D-mannitol, 2N-acetylamino-D-mannitol, L-rhamnitol, or D-fucitol; or a combination thereof; optionally a carrier; and optionally a diluent. It is a further object of the invention that the bacteria which causes the disease can be *Streptococcus* spp., *Enterococcus* spp., and/or *Bacillus* spp. It is another object of this invention that the composition is applied topically, orally, or parenterally to the animal. It is another object of this invention that the animal can be a mammal, a bird, a fish, an amphibian, or a reptile.

It is another object of this invention to have a method of treating a disease caused by a bacterial infection in an animal having said disease by administering a therapeutically effective amount of a composition to the animal having the disease, the amount being effective to kill the bacteria causing the disease, and the composition contains optionally a carrier, optionally a diluent, and one or more of L-mannitol liamocin A1, L-mannitol liamocin A2, L-mannitol liamocin B1, L-mannitol liamocin B2, D-mannitol liamocin A1, D-mannitol liamocin A2, D-mannitol liamocin B1, D-mannitol liamocin B2, L-arabitol liamocin A1, L-arabitol liamocin A2, L-arabitol liamocin B1, L-arabitol liamocin B2, D-arabitol liamocin A1, D-arabitol liamocin A2, D-arabitol liamocin B1, D-arabitol liamocin B2, L-threitol liamocin A1, L-threitol liamocin A2, L-threitol liamocin B1, L-threitol liamocin B2, D-threitol liamocin A1, D-threitol liamocin A2, D-threitol liamocin B1, D-threitol liamocin B2, L-glycerol liamocin A1, L-glycerol liamocin A2, L-glycerol liamocin B1, L-glycerol liamocin B2, D-glycerol liamocin A1, D-glycerol liamocin A2, D-glycerol liamocin B1, and D-glycerol liamocin B2. It is a further object of the invention that the bacteria which causes the disease can be *Streptococcus* spp., *Enterococcus* spp., and/or *Bacillus* spp. It is another object of this invention that the composition is applied topically, orally, or parenterally to the animal. It is another object of this invention that the animal can be a mammal, a bird, a fish, an amphibian, or a reptile.

Another object of this invention is a method of preventing a disease caused by bacteria in an animal susceptible to the disease by administering an effective amount of a composition to prevent the growth of bacteria in or on the animal, and the composition contains optionally a carrier, optionally a diluent, and one or more isolated and purified oils having the chemical structure of Formula 1

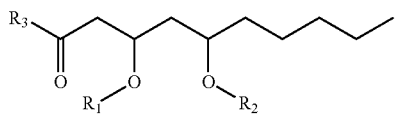

Formula 1 where $R_1$ is, independently, either $COCH_3$ or H; and $R_2$ is, independently, between two to ten O-linked 3,5-dihydroxydecanoate; and $R_3$ is, independently, one of the following: L- or D-glycerol, L- or D-threitol, L- or D-erythritol, L- or D-arabitol, L- or D-xylitol, L- or D-lyxitol, L- or D-ribitol, L- or D-allitol, L- or D-altritol, L- or D-mannitol, L- or D-iditol, L- or D-gulitol, L- or D-glucitol, L- or D-galactitol, L- or D-talitol, 2-amino-D-mannitol, 2N-acetylamino-D-mannitol, L-rhamnitol, or D-fucitol; or a combination thereof. It is a further object of the invention that the bacteria which causes the disease can be *Streptococcus* spp., *Enterococcus* spp., and/or *Bacillus* spp. It is another object of this invention that the composition is applied topically, orally, or parenterally to the animal. It is another object of this invention that the animal can be a mammal, a bird, a fish, an amphibian, or a reptile.

Another object of this invention is a method of preventing a disease caused by bacteria in an animal susceptible to the disease by administering an effective amount of a composition to prevent the growth of bacteria in or on the animal, and the composition contains optionally a carrier, optionally a diluent, and one or more of L-mannitol liamocin A1, L-mannitol liamocin A2, L-mannitol liamocin B1, L-mannitol liamocin B2, D-mannitol liamocin A1, D-mannitol liamocin A2, D-mannitol liamocin B1, D-mannitol liamocin B2, L-arabitol liamocin A1, L-arabitol liamocin A2, L-arabitol liamocin B1, L-arabitol liamocin B2, D-arabitol liamocin A1, D-arabitol liamocin A2, D-arabitol liamocin B1, D-arabitol liamocin B2, L-threitol liamocin A1, L-threitol liamocin A2, L-threitol liamocin B1, L-threitol liamocin B2, D-threitol liamocin A1, D-threitol liamocin A2, D-threitol liamocin B1, D-threitol liamocin B2, L-glycerol liamocin A1, L-glycerol liamocin A2, L-glycerol liamocin B1, L-glycerol liamocin B2, D-glycerol liamocin A1, D-glycerol liamocin A2, D-glycerol liamocin B1, and D-glycerol liamocin B2. It is a further object of the invention that the bacteria which causes the disease can be *Streptococcus* spp., *Enterococcus* spp., and/or *Bacillus* spp. It is another object of this invention that the composition is applied topically, orally, or parenterally to the animal. It is another object of this invention that the animal can be a mammal, a bird, a fish, an amphibian, or a reptile.

It is a further object of this invention to have a method of preventing the growth of bacteria on a surface by applying to the surface an effective amount of a composition that prevents the growth the bacteria, and the composition contains optionally a carrier, optionally a diluent, and one or more isolated and purified oils having the chemical structure of Formula 1

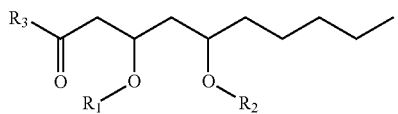

Formula 1 where $R_1$ is, independently, either $COCH_3$ or H; and $R_2$ is, independently, between two to ten O-linked 3,5-dihydroxydecanoate; and $R_3$ is, independently, one of the following: L- or D-glycerol, L- or D-threitol, L- or D-erythritol, L- or D-arabitol, L- or D-xylitol, L- or D-lyxitol, L- or D-ribitol, L- or D-allitol, L- or D-altritol, L- or D-mannitol, L- or D-iditol, L- or D-gulitol, L- or D-glucitol, L- or D-galactitol, L- or D-talitol, 2-amino-D-mannitol, 2N-acetylamino-D-mannitol, L-rhamnitol, or D-fucitol; or a combination thereof. It is another object of the invention that the bacteria to be prevented from growing on the surface are *Streptococcus* spp., *Enterococcus* spp., and/or *Bacillus* spp.

It is yet another object of this invention to have a method of preventing the growth of bacteria on a surface by applying to the surface an effective amount of a composition that prevents the growth the bacteria, and the composition contains optionally a carrier, optionally a diluent, and one or more of L-mannitol liamocin A1, L-mannitol liamocin A2, L-mannitol liamocin B1, L-mannitol liamocin B2, D-mannitol liamocin A1, D-mannitol liamocin A2, D-mannitol liamocin B1, D-mannitol liamocin B2, L-arabitol liamocin A1, L-arabitol liamocin A2, L-arabitol liamocin B1, L-arabitol liamocin B2, D-arabitol liamocin A1, D-arabitol liamocin A2, D-arabitol liamocin B1, D-arabitol liamocin B2, L-threitol liamocin A1, L-threitol liamocin A2, L-threitol liamocin B1, L-threitol liamocin B2, D-threitol liamocin A1, D-threitol liamocin A2, D-threitol liamocin B1, D-threitol liamocin B2, L-glycerol liamocin A1, L-glycerol liamocin A2, L-glycerol liamocin B1, L-glycerol liamocin B2, D-glycerol liamocin A1, D-glycerol liamocin A2, D-glycerol liamocin B1, and D-glycerol liamocin B2. It is an object of the invention that the bacteria to be prevented from growing on the surface are *Streptococcus* spp., *Enterococcus* spp., and/or *Bacillus* spp.

It is an object of this invention to have a method of killing bacteria growing on a surface by applying to the surface an effective amount of a composition to kill the bacteria, and the composition contains optionally a carrier, optionally a diluent, and one or more isolated and purified oils having the chemical structure of Formula 1

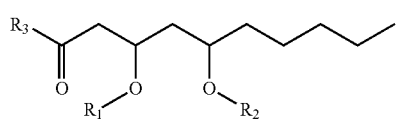

Formula 1 where $R_1$ is, independently, either $COCH_3$ or H; and $R_2$ is, independently, between two to ten O-linked 3,5-dihydroxydecanoate; and $R_3$ is, independently, one of the following: L- or D-glycerol, L- or D-threitol, L- or D-erythritol, L- or D-arabitol, L- or D-xylitol, L- or D-lyxitol, L- or D-ribitol, L- or D-allitol, L- or D-altritol, L- or D-mannitol, L- or D-iditol, L- or D-gulitol, L- or D-glucitol, L- or D-galactitol, L- or D-talitol, 2-amino-D-mannitol, 2N-acetylamino-D-mannitol, L-rhamnitol, or D-fucitol; or a combination thereof. It is another object of the invention that the bacteria to be killed are *Streptococcus* spp., *Enterococcus* spp., and/or *Bacillus* spp.

It is an object of this invention to have a method of killing bacteria growing on a surface by applying to the surface an effective amount of a composition to kill the bacteria, and the composition contains optionally a carrier, optionally a diluent, and one or more of L-mannitol liamocin A1, L-mannitol liamocin A2, L-mannitol liamocin B1, L-mannitol liamocin B2, D-mannitol liamocin A1, D-mannitol liamocin A2, D-mannitol liamocin B1, D-mannitol liamocin B2, L-arabitol liamocin A1, L-arabitol liamocin A2, L-arabitol liamocin B1, L-arabitol liamocin B2, D-arabitol liamocin A1, D-arabitol liamocin A2, D-arabitol liamocin B1, D-arabitol liamocin B2, L-threitol liamocin A1, L-threitol liamocin A2, L-threitol liamocin B1, L-threitol liamocin B2, D-threitol liamocin A1, D-threitol liamocin A2, D-threitol liamocin B1, D-threitol liamocin B2, L-glycerol liamocin A1, L-glycerol liamocin A2, L-glycerol liamocin B1, L-glycerol liamocin B2, D-glycerol liamocin A1, D-glycerol liamocin A2, D-glycerol liamocin B1, and D-glycerol liamocin B2. It is an object of the invention that the bacteria to be killed are *Streptococcus* spp., *Enterococcus* spp., and/or *Bacillus* spp.

It is a further object of this invention to have a novel and isolated *Aureobasidium pullulans* strain capable of producing liamocin. It is another object of this invention that the *A. pullulans* strain can be *A. pullulans* strain CU 43 (NRRL 50380), *A. pullulans* strain RSU 12 (NRRL 50381), *A. pullulans* strain RSU 32 (NRRL 50382), *A. pullulans* strain RSU 6 (NRRL 50383), and/or *A. pullulans* RSU 29 (NRRL 50384).

It is yet a further object of this invention to have a method of producing arabitol-liamocins by culturing *Aureobasidium pullulans* on media containing arabitol as a carbon source. It is yet another object of this invention that the *A. pullulans* strain can be *A. pullulans* strain CU 43 (NRRL 50380), *A. pullulans* strain RSU 12 (NRRL 50381), *A. pullulans* strain RSU 32 (NRRL 50382), *A. pullulans* strain RSU 6 (NRRL 50383), and/or *A. pullulans* RSU 29 (NRRL 50384).

It is an object of this invention to have a method for producing threitol-liamocins by culturing *Aureobasidium pullulans* on a media containing L-threitol as a carbon source. It is yet another object of this invention that the *A. pullulans* strain can be *A. pullulans* strain CU 43 (NRRL 50380), *A. pullulans* strain RSU 12 (NRRL 50381), *A. pullulans* strain RSU 32 (NRRL 50382), *A. pullulans* strain RSU 6 (NRRL 50383), and/or *A. pullulans* RSU 29 (NRRL 50384).

DETAILED DESCRIPTION OF THE INVENTION

Figure 1A:
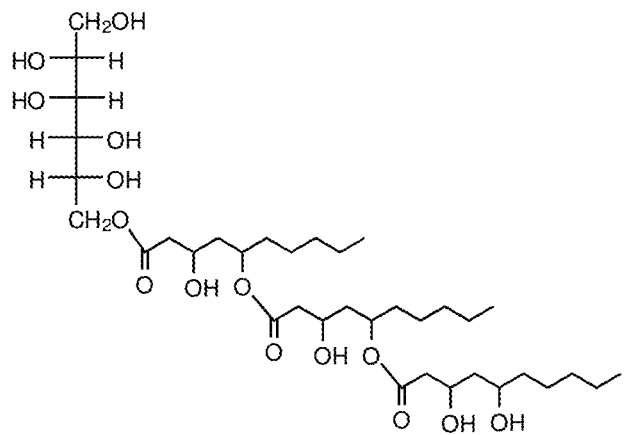
FIG. 1A shows the structure of D-mannitol-liamocin A1 (Formula 41; D-mannitol liamocin trimer).

Declaration Regarding Deposit of Biological Materials Under the Budapest Treaty

On Jun. 1, 2010, we, the inventors of the invention described herein, affirm that we deposited five samples of *Aureobasidium pullulans* with the U.S.D.A., Agricultural Research Service Patent Culture Collection located at the National Center for Agricultural Utilization Research, 1815 N. University Street, Peoria, Ill. 61604, in a manner affording permanence of the deposits and ready accessibility thereto by the public if a patent is granted. *A. pullulans* strain CU 43 was accorded deposit number NRRL 50380; *A. pullulans* strain RSU 12 was accorded deposit number NRRL 50381; *A. pullulans* strain RSU 32 was accorded deposit number NRRL 50382; *A. pullulans* strain RSU 6 was accorded deposit number NRRL 50383; and *A. pullulans* strain RSU 29 was accorded deposit number NRRL 50384. These deposits were made under the terms of the Budapest Treaty on the International Recognition of the Deposit of Microorganisms for the Purposes of Patent Procedure and the regulations thereunder.

All restrictions on the availability to the public of *A. pullulans* ARS Patent Culture Collection Accession Numbers NRRL 50380, NRRL 50381, NRRL 50382, NRRL 50383, and NRRL 50384 will be irrevocably removed upon the granting of a patent.

*A. pullulans* ARS Patent Culture Collection Accession Numbers NRRL 50380, NRRL 50381, NRRL 50382, NRRL 50383, and NRRL 50384 were deposited under conditions such that access to the microorganisms are available during the pendency of the patent application to one determined by the Commissioner to be entitled thereto under 37 C.F.R. § 1.14 and 35 U.S.C § 122.

The deposited biological materials will be maintained with all the care necessary to keep them viable and uncontaminated for a period of at least five years after the most recent request for the furnishing of a sample of the deposited microorganism, and in any case, for a period of at least thirty (30) years after the date of deposit for the enforceable life of the patent, whichever period is longer.

The present invention relates to the compounds and/or compositions containing the compounds described herein and the use of them to kill or inhibit the growth of *Streptococcus* spp., and other bacteria susceptible to the compounds of this invention. The present invention also covers the use of these compounds and/or compositions described herein as a disinfectant to kill or inhibit the growth of *Streptococcus* spp., and other bacteria susceptible to the compounds of this invention on the surface of an animal or surface of an item, such as, but not limited to, a counter, wall, floor, an instrument (medical or veterinarian), a fruit, a vegetable, and other types of food (pieces of meat, fish, etc.). Non-limiting examples of diseases caused by *Streptococcus* spp. include mastitis, strep throat, otitis media, pneumonia, upper respiratory infections, wound infections, puerperal fever, scarlet fever, rheumatic fever, septicemia, toxic shock syndrome, necrotizing fasciitis, sepsis, meningitis, peritonitis, sinusitis, pink eye, endocarditis, erysipelas, dental caries, strangles, pharyngitis, meningoencephalitis, skin lesions, and osteomyelitis.

In particular, the novel compounds of this invention are called liamocins and are provided in Formula 1:

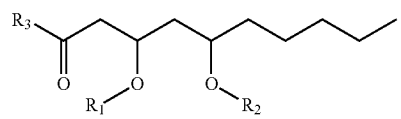

Formula 1 where $R_1$ is, independently, either $COCH_3$ or H; and $R_2$ is, independently, between two to ten O-linked 3,5-dihydroxydecanoate; and $R_3$ is, independently, one of the following: L- or D-glycerol, L- or D-threitol, L- or D-erythritol, L- or D-arabitol, L- or D-xylitol, L- or D-lyxitol, L- or D-ribitol, L- or D-allitol, L- or D-altritol, L- or D-mannitol, L- or D-iditol, L- or D-gulitol, L- or D-glucitol (also called sorbitol), L- or D-galactitol (also called dulcitol), L- or D-talitol, 2-amino-D-mannitol, 2N-acetylamino-D-mannitol, L-rhamnitol, or D-fucitol; except when $R_3$ is D-mannitol, $R_2$ is not 2 nor 3 O-linked 3,5-dihydroxydecanoate chains, and homologs thereof. In particular, a subset of the novel compounds described in Formula 1 above are described in the following formulas:

Formula 2

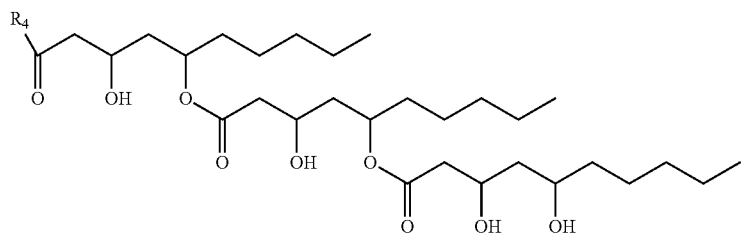

(general formula for liamocin A1)

Formula 3

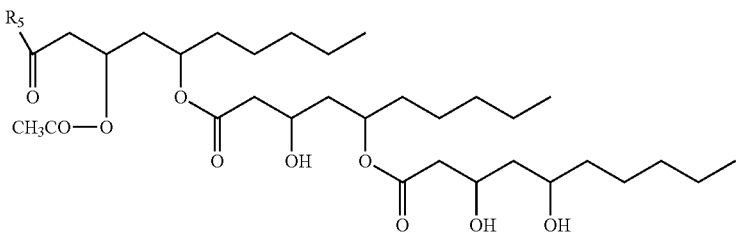

(general formula for liamocin A2)

Formula 4

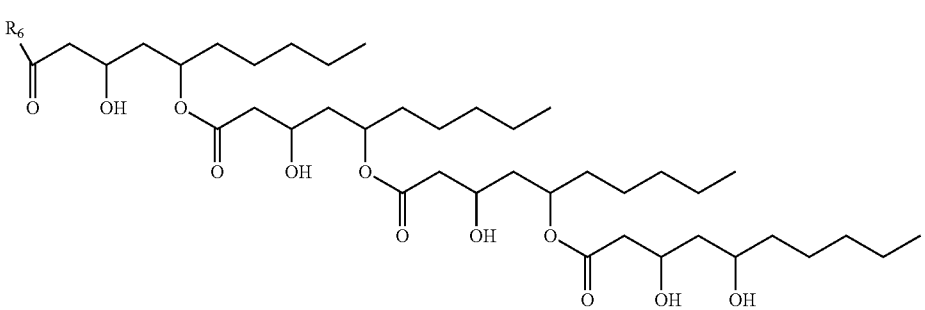

(general formula for liamocin B1) ; or

Formula 5

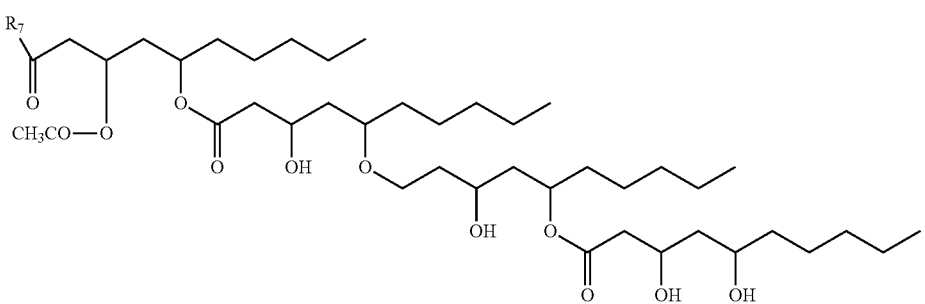

(general formula for liamocin B2)

where $R_4$, $R_5$, $R_6$, and $R_7$ can independently be any of the following which are attached to Formula 2, Formula 3, Formula 4, or Formula 5 via an ester bond at the $C_2HO$:

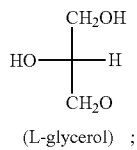

Formula 6

(L-glycerol);

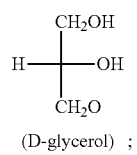

Formula 7

(D-glycerol);

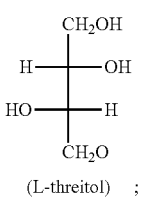

Formula 8

(L-threitol);

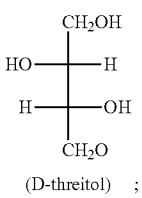

Formula 9

(D-threitol);

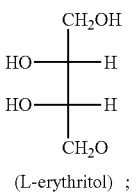

Formula 10

(L-erythritol);

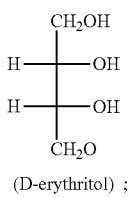

Formula 11

(D-erythritol);

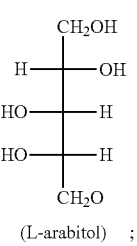

Formula 12

(L-arabitol);

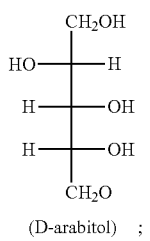

Formula 13

(D-arabitol);

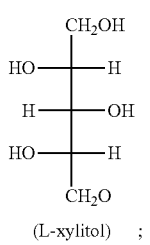

Formula 14

(L-xylitol);

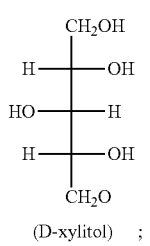

Formula 15

(D-xylitol);

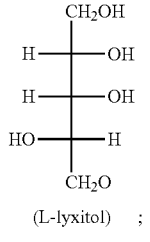

Formula 16

(L-lyxitol);

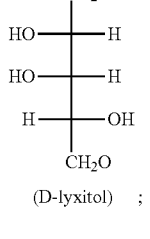

Formula 17

(D-lyxitol);

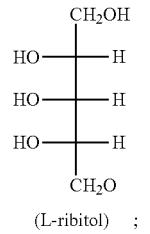

Formula 18

(L-ribitol);

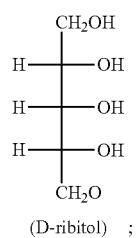
(D-ribitol)  ;  Formula 19
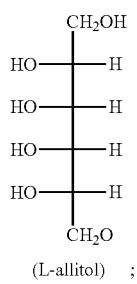
(L-allitol)  ;  Formula 20
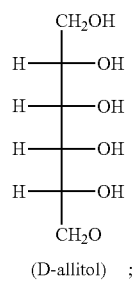
(D-allitol)  ;  Formula 21
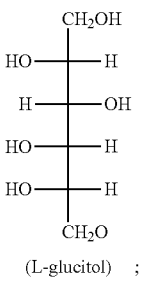
(L-glucitol)  ;  Formula 22
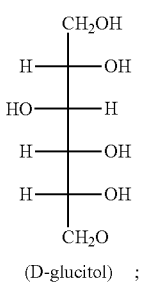
(D-glucitol)  ;  Formula 23
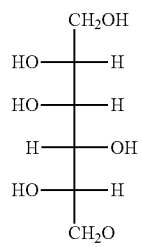
(L-gulitol)  ;  Formula 24
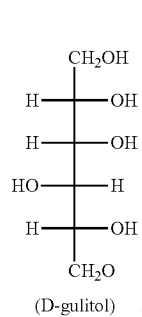
(D-gulitol)  ;  Formula 25
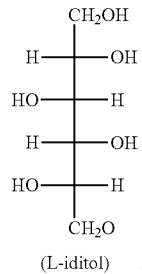
(L-iditol)  ;  Formula 26
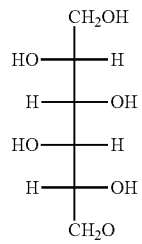
(D-iditol)  ;  Formula 27
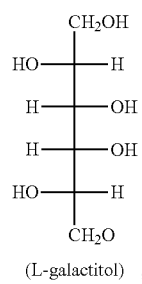
(L-galactitol)  ;  Formula 28

Formula 29
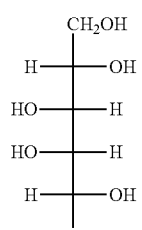
(D-galactitol);
Formula 30
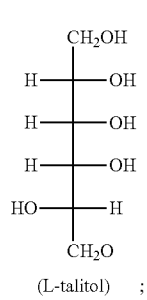
(L-talitol);
Formula 31
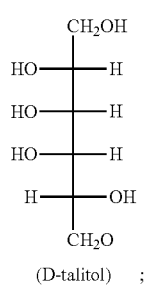
(D-talitol);
Formula 32
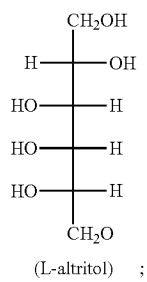
(L-altritol);
Formula 33
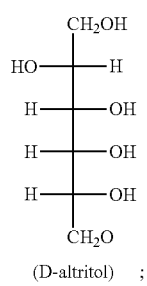
(D-altritol);
Formula 34
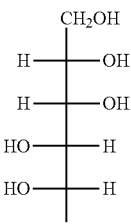
(L-mannitol);
Formula 35
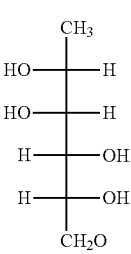
(D-fucitol);
Formula 36
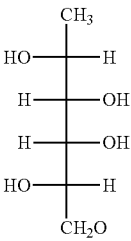
(L-rhamnitol);
Formula 37
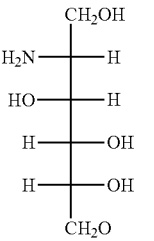
(2-amino-D-mannitol); and
Formula 38
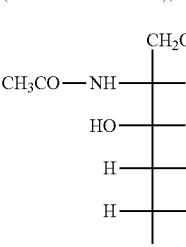
(2-N-acetylamino-D-mannitol).

In addition the novel compounds of this invention include

Formula 39

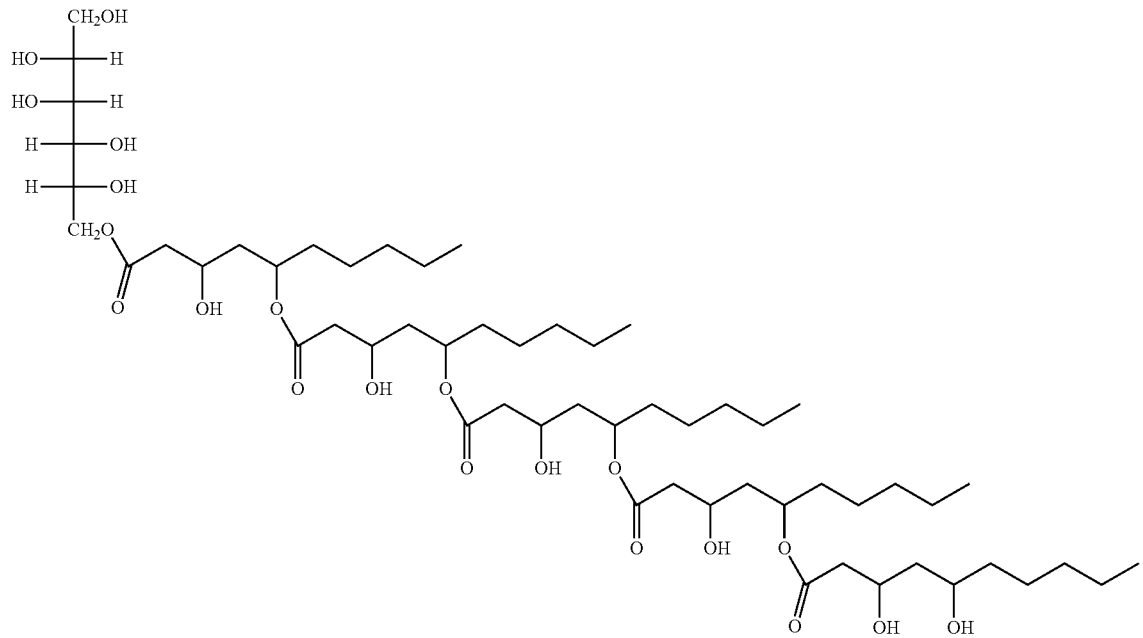

(D-mannitol liamocin pentamer; D-mannitol liamocin C1) and

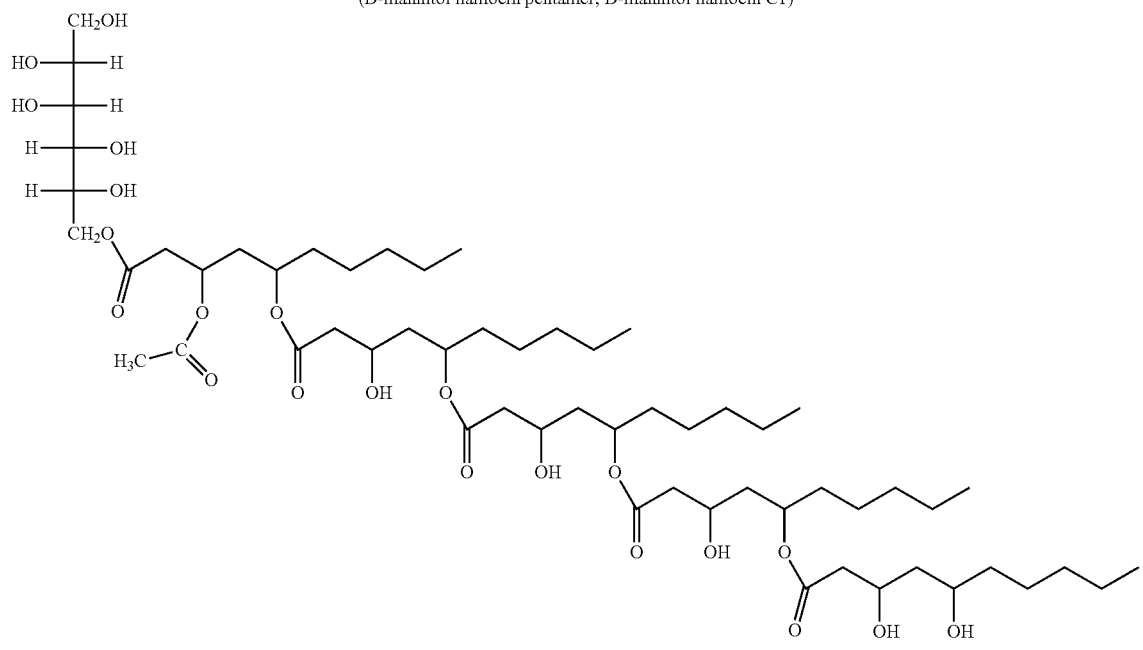

(3-O-acetyl-D-mannitol liamocin pentamer; D-mannitol liamocin C2).

To be clear, D-mannitol liamocin pentamer (Formula 39; D-mannitol liamocin C1) is described by Formula 1, where $R_1$ is H, $R_2$ is four O-linked 3,5-dihydroxydecanoate, and $R_3$ is D-mannitol. Similarly, 3-O-acetyl-D-mannitol liamocin pentamer (Formula 40, D-mannitol liamocin C2) is described by Formula 1, where $R_1$ is COCH$_3$, $R_2$ is four O-linked 3,5-dihydroxydecanoate, and $R_3$ is D-mannitol. To assist in understanding the nomenclature of the compounds described herein, the following is provided as a general guideline. "Arabitol-liamocin trimer" (Formula 2 where $R_4$ is either Formula 12 or Formula 13) is also referred to as "arabitol-liamocin A1", "ara-liamocin A1", or "ara-A1". "3-O-acetyl-arabitol-liamocin trimer" (Formula 3 where $R_5$ is either Formula 12 or Formula 13) is also referred to as "arabitol-liamocin A2", "ara-liamocin A2", or "ara-A2". "Arabitol-liamocin tetramer" (Formula 4 where $R_6$ is either Formula 12 or Formula 13) is also referred to as "arabitol-liamocin B1", "ara-liamocin B1", or "ara-B1". "3-O-acetyl-arabitol-liamocin tetramer" (Formula 5 where $R_7$ is either Formula 12 or Formula 13) is also referred to as "arabitol-liamocin B2", "ara-liamocin B2", or "ara-B2". "Arabitol-liamocin pentamer" (Formula 1 where $R_1$ is H, $R_2$ is four O-linked 3,5-dihydroxydecanoate, and $R_3$ is arabitol) is also referred to as "arabitol-liamocin C1", "ara-liamocin C1", or "ara-C1". "3-O-acetyl-arabitol-liamocin pentamer" (Formula 1 where $R_1$ is $COCH_3$, $R_2$ is four O-linked 3,5-dihydroxydecanoate, and $R_3$ is arabitol) is also referred to as "arabitol-liamocin C2", "ara-liamocin C2", or "ara-C2". This nomenclature works for liamocin compound having any head group listed as $R_3$ for Formula 1 (with $R_1$ being, independently, either H or $COCH_3$; and $R_2$ being, independently, 2 to 10 O-linked 3,5-dihydroxydecanoate) or for any head group listed as $R_4$, $R_5$, $R_6$, or $R_7$ (i.e., Formulas 6-38) for any of Formulas 2, 3, 4, or 5.

Figure 1B:
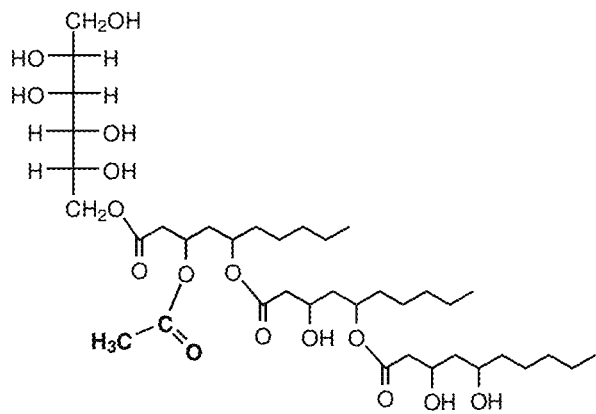
FIG. 1B shows the structure of D-mannitol-liamocin A2 (Formula 42; 3-O-acetyl-D-mannitol liamocin trimer).
Figure 1C:
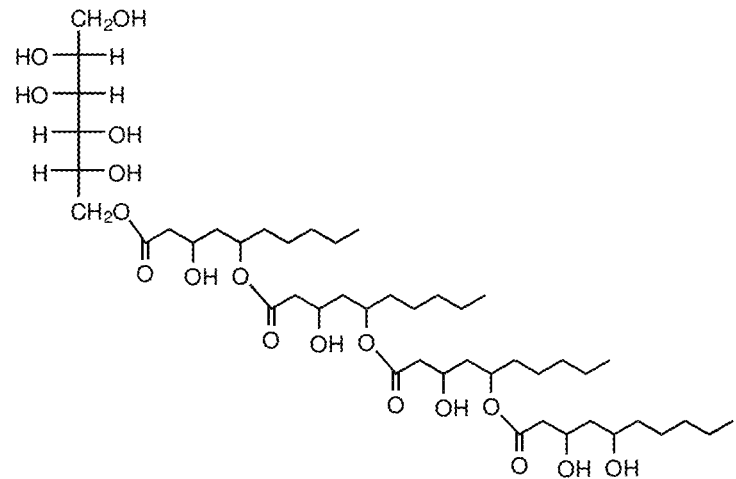
FIG. 1C shows the structure of D-mannitol-liamocin B1 (Formula 43; D-mannitol liamocin tetramer).
Figure 1D:
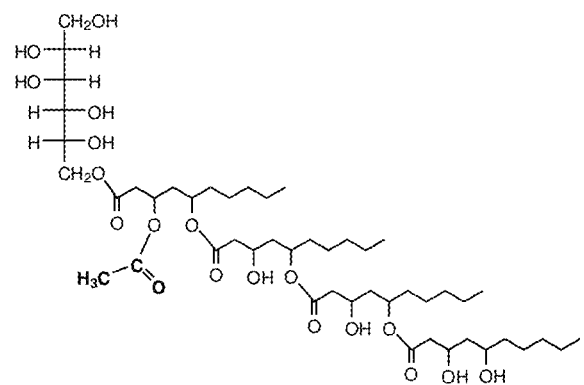
FIG. 1D shows the structure of D-mannitol-liamocin B2 (Formula 44; 3-O-acetyl-D-mannitol liamocin tetramer).

The compounds of this invention (liamocins) described in Formula 1 where $R_1$ is either, independently, $COCH_3$ or H; and $R_2$ is, independently, between two to ten O-linked 3,5-dihydroxydecanoate; and $R_3$ is, independently, one of the following: L- or D-glycerol, L- or D-threitol, L- or D-erythritol, L- or D-arabitol, L- or D-xylitol, L- or D-lyxitol, L- or D-ribitol, L- or D-allitol, L- or D-altritol, L- or D-mannitol, L- or D-iditol, L- or D-gulitol, L- or D-glucitol (also called sorbitol), L- or D-galactitol (also called dulcitol), L- or D-talitol, 2-amino-D-mannitol, 2N-acetylamino-D-mannitol, L-rhamnitol, or D-fucitol; individually or in combination with each other, and optionally in compositions with other components, have antibacterial activity and are used to kill bacteria susceptible to the liamocins. To be clear, the use of D-mannitol liamocin A1 (Formula 41, D-mannitol liamocin trimer), D-mannitol liamocin A2 (Formula 42; 3-O-acetyl-D-mannitol liamocin trimer), D-mannitol liamocin B1 (Formula 43; D-mannitol liamocin tetramer), and D-mannitol liamocin B2 (Formula 44; 3-O-acetyl-D-mannitol liamocin trimer) (FIG. 1) to kill bacteria has not been previously reported and thus is included in the methods described herein. The term "liamocin" can refer to any of the structures above, unless there is explicit language indicating that one or more particular compounds within the liamocin family is/are being excluded. Of the compounds covered by Formula 1, a subset of these compounds which are described in Formulas 2, 3, 4, and 5 where $R_4$, $R_5$, $R_6$, and $R_7$ can independently be any of Formulas 6 through 38 can be used as antibacterial agents. Also useful as antibacterial agents are the novel compounds in Formula 39 (D-mannitol liamocin pentamer, liamocin C1) and Formula 40 (3-O-acetyl-D-mannitol liamocin pentamer, liamocin C2), and the previously described compounds of D-mannitol liamocin A1 trimer (Formula 41 in FIG. 1), D-mannitol liamocin A2 (Formula 42 in FIG. 1B), D-mannitol liamocin B1 (Formula 43 in FIG. 1C), and D-mannitol liamocin B2 (Formula 44 in FIG. 1D).

The liamocins or compositions containing liamocins can be applied topically, orally, rectally, or parenterally to an animal to prevent or kill the growth of *Streptococcus* spp., *Enterococcus* spp., and/or *Bacillus* spp., or specific species of *Streptococcus, Enterococcus*, and/or *Bacillus*, and thus prevent or treat diseases caused by the bacteria. The liamocins or compositions containing one or more liamocin can also be used as a disinfectant, applied to surfaces to prevent the growth of and/or kill *Streptococcus* spp., *Enterococcus* spp., and/or *Bacillus* spp. or specific species of thereof. In one embodiment, the compositions containing one or more of the liamocins described herein do not contain *A. pullulans* because the liamocins have been isolated and purified from *A. pullulans*. "Isolated and purified" when referring to a compound (liamocin) means that the compound in question (liamocin) is removed from the organism that produced it (*A. pullulans*). Because *A. pullulans* secretes liamocin, the removal of the oil (liamocin) from the cultured organism results in the isolation and purification of liamocin. One can further purify liamocin to remove other compounds that are present within the oil in minor amounts.

A "therapeutically effective amount" or "effective amount" or "effective dose" of an active agent is a dose sufficient to either prevent or treat a disease in an animal to which the active agent is administered or to prevent or treat a bacterial infection caused by *Streptococcus* spp., *Enterococcus* spp., and/or *Bacillus* spp., or other bacteria susceptible to the compounds of this invention in or on an animal, including human. The therapeutically effective amount of the active agent which can treat or prevent a bacterial infection can be determined by one of ordinary skill in the art by running routine trials with appropriate controls. The liamocins and/or compositions containing one or more liamocin are administered in an amount effective to control the population(s) of the target bacteria in or on animals and surfaces of items. The effective amount will also significantly reduce or eliminate the population(s) of the target bacteria, and/or reduce the incidence of infection by these bacteria, in and/or on a treated animal in comparison to untreated control animal. Comparison of the appropriate treatment groups to the controls will indicate whether a particular dosage of the compounds of this invention is effective in preventing or treating the bacterial infection, and thus is a therapeutically effective amount. It is understood in the art that the amount of the active agent administered or applied to the animal should be the amount that is effective to control the particular pathogen or pathogens in question. In addition, the type, size and condition of the animal being treated must be taken into consideration. For example, when controlling a pathogen responsible for mastitis, the therapeutically effective amount of the compounds of this invention will vary depending on the type and size of the mammal (e.g., ruminant) being treated. Yet, that therapeutically effective amount may differ from an effective dose to prevent infection from *Streptococcus* spp., *Enterococcus* spp., and/or *Bacillus* spp., or other susceptible bacteria in a human. Also, when determining the effective dose, one should consider the age, body weight, general health, sex and diet of the animal, the time of administration, the route of administration, the rate of excretion of the compound or composition of this invention, the duration of the treatment, drugs or other compounds used in combination or coincidental with the administration of the compound or compositions of this invention, and other well known in the field. A therapeutically effective amount may be achieved by a single dose or multiple doses.

Treatment is the medical management of an animal, including human, with the intent to cure, ameliorate, stabilize, or prevent a disease, infection, pathological condition, or disorder. "Treatment" includes (i) active treatment, that is, treatment directed specifically toward the improvement of a disease, infection, pathological condition, or disorder; (ii) causal treatment, that is, treatment directed toward removal of the cause of the associated disease, infection, pathological condition, or disorder; (iii) palliative treatment, that is, treatment designed for the relief of symptoms rather than the curing of the disease, infection, pathological condition, or disorder; (iv) preventative treatment, that is, treatment directed to minimizing or partially or completely inhibiting the development of the associated disease, infection, pathological condition, or disorder; and (v) supportive treatment, that is, treatment employed to supplement another specific therapy directed toward the improvement of the associated disease, pathological condition, or disorder.

Exemplary administration of the liamocins or compositions containing one or more liamocin can be a relatively short-term period lasting approximately one or approximately two days, approximately one or approximately two weeks, or approximately one, approximately two or even approximately three months. Exemplary administration of the liamocins or compositions containing one or more liamocin can be a relatively long-term period lasting from approximately three or approximately four months to approximately one year, or even longer. In one embodiment, the suitable dosages of the liamocin and compositions containing one or more liamocin described herein can range from approximately 0.01 mg/day/kg to approximately 10 g/day/kg of the body weight of the animal to which the compounds and/or compositions are applied or administered. In another embodiment, the suitable dosages of the liamocins and compositions containing one or more liamocin described herein can range from approximately 0.1 mg/day/kg to approximately 1 g/day/kg of the body weight of the animal to which the compounds and/or compositions are applied or administered. In yet another embodiment, the suitable dosage can range from approximately 1 mg/day/kg to approximately 500 mg/day/kg of body weight.

The liamocins and compositions containing one or more liamocin may be administered to or applied onto an animal directly. In another embodiment, the compounds and compositions may be mixed with an animal's feed or water. In yet another embodiment, the liamocins and compositions containing one or more liamocin may be further formulated with a carrier (pharmaceutically or veterinarianly acceptable carrier) to facilitate administration.

The carrier can take a wide variety of forms depending on the form of preparation desired for administration, e.g., oral or parenteral (including intravenous), or application, e.g., applied topically or on the surface. The compositions of the present invention can be presented as discrete units suitable for oral administration, such as capsules, cachets or tablets each containing a predetermined amount of the compound(s) of this invention. Further, the compositions can be presented as a powder, as a cream, as an ointment, as granules, as a solution, as a suspension in an aqueous liquid, as a non-aqueous liquid, as an oil-in-water emulsion or as a water-in-oil liquid emulsion. In addition to the common dosage forms set out above, the liamocins and/or the compositions containing one or more liamocin can also be administered by controlled release devices or compositions and/or delivery devices. The compositions can be prepared by any of the methods known to one of skill in the art. In general, such methods include a step of bringing into association the compound(s) with the carrier that constitutes one or more necessary ingredients. In general, the compositions are prepared by uniformly and intimately admixing the compound(s) with liquid carriers or finely divided solid carriers or both. The product can then be conveniently shaped into the desired presentation.

In preparing the compositions for oral dosage form, any convenient pharmaceutical or veterinarian diluents can be employed. For example, water, glycols, oils, alcohols, flavoring agents, preservatives, coloring agents and the like can be used to form oral liquid preparations such as suspensions, elixirs and solutions; while carriers such as starches, sugars, microcrystalline cellulose, diluents, granulating agents, lubricants, binders, disintegrating agents, and the like can be used to form oral solid preparations such as powders, capsules and tablets. Optionally, tablets can be coated by standard aqueous or non-aqueous techniques. Non-limited examples of carriers include lactose, dextrose, sucrose, sorbitol, mannitol, starch, acacia gum, calcium phosphate, alginate, gelatin, calcium silicate, microcrystalline cellulose, polyvinylpyrrolidone, cellulose, water, syrup, methyl cellulose, methyl hydroxy benzoate, propyl hydroxy benzoate, talc, stearic acid, magnesium, and mineral oils. Suitable carriers and formulations are described in detail in *Remington's Pharmaceutical Sciences* (19th ed., 1995).

Compositions of the present invention suitable for parenteral administration can be prepared as solutions or suspensions or emulsions or dispersions of the active compounds in water or other liquid. A suitable surfactant can be included; such as, for example, hydroxypropylcellulose. The compounds can also be prepared in glycerol, liquid polyethylene glycols, and mixtures thereof in oils. Further, a preservative can be included to prevent the detrimental growth of microorganisms.

If applicable, a tablet containing the composition of this invention can be prepared by compression or molding, optionally with one or more accessory ingredients or adjuvants. Compressed tablets can be prepared by compressing, in a suitable machine, the compound(s) of the invention in a free-flowing form such as powder or granules, optionally mixed with a binder, lubricant, inert diluent, surface active or dispersing agent. Molded tablets can be made by molding in a suitable machine, a mixture of the powdered compound moistened with an inert liquid diluent.

Compositions of the present invention suitable for injectable use include sterile aqueous solutions or dispersions. Furthermore, the compositions can be in the form of sterile powders for the extemporaneous preparation of such sterile injectable solutions or dispersions. In all cases, the final injectable form must be sterile and must be effectively fluid for easy syringability. The pharmaceutical compositions must be stable under the conditions of manufacture and storage; thus, preferably should be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), vegetable oils, and suitable mixtures thereof.

Compositions of the present invention can be in a form suitable for topical use such as, for example, an aerosol, cream, ointment, lotion, dusting powder, mouth washes, gargles, and the like. Further, the compositions can be in a form suitable for use in transdermal devices. These formulations can be prepared, utilizing the compound(s) of the invention via conventional processing methods. As an example, a cream or ointment is prepared by mixing hydrophilic material and water, together with about 5 wt % to about 10 wt % of the compound(s) to produce a cream or ointment having a desired consistency.

As a disinfectant agent, the compound(s) can be made into a solution, suspension, gel, or spray that can be wiped on, sprayed on, poured on, etc., onto a surface. It also can be a solution, suspension, or gel into which a body part or object is dipped. It can also be made into a solution, suspension, gel, or similar type of compound that can be applied to an object or animal or part of an animal. Such disinfecting solutions, suspensions, gels, or sprays containing one or more liamocin or the isolated liamocin-containing oil can be applied to medical or veterinarian instruments, especially those for which are sensitive to extreme heat and/or pressure and thus would be damaged by autoclaving. In such disinfectant solutions, suspensions, gels, or sprays, the amount of each liamocin, combination of liamocins, or isolated liamocin-containing oil can range between approximately 0.001 µg/ml to approximately 1 g/ml in one embodiment, between approximately 0.01 µg/ml to approximately 100 mg/ml in another embodiment, between approximately 0.1 µg/ml to approximately 10 mg/ml in another embodiment, or between approximately 1 µg/ml to approximately 1 mg/ml in another embodiment.

One type of disinfecting solution or suspension can be a mouthwash. Such a mouthwash may have one or more of the following ingredients water, phenol, thymol, eugenol, eucalyptol, menthol, alcohol, chlorhexidine gluconate, cetylpyridinium chloride, hexetidine, benzoic acid, methyl salicylate, triclosan, benzalkonium chloride, methylparaben, hydrogen peroxide, domiphen bromide and/or fluoride. Some mouthwashes also include sweeteners, such as sorbitol, sucralose, sodium saccharin, and xylitol. The amount of *A. pullulans* oil or one or more liamocin described herein, including D-mannitol liamocin A1, D-mannitol liamocin A2, D-mannitol liamocin B1, and D-mannitol liamocin B2, and those described by Formula 39, Formula 40, and Formula 1, and in particular described by Formulas 2, 3, 4, and 5 where $R_4$, $R_5$, $R_6$, and $R_7$ can independently be any of Formulas 6-38, (alone or in combination with one of more of each other) can range from between approximately 0.001 µg/ml to approximately 1 g/ml in one embodiment, between approximately 0.01 µg/ml to approximately 100 mg/ml in another embodiment, between approximately 0.1 µg/ml to approximately 10 mg/ml in another embodiment, or between approximately 1 µg/ml to approximately 1 mg/ml in another embodiment.

Compositions of this invention can be in a form suitable for rectal administration where the carrier is a solid that dissolves at body temperature. It is preferable that the mixture forms unit dose suppositories. Suitable carriers include cocoa butter and other materials commonly used in the art. The suppositories can be conveniently formed by first admixing the composition with the softened or melted carrier(s) followed by chilling and shaping in molds.

In addition to the aforementioned carrier ingredients, the formulations described above can include, as appropriate, one or more additional carrier ingredients such as diluents, buffers, flavoring agents, binders, surface-active agents, thickeners, lubricants, preservatives (including anti-oxidants) and the like. Furthermore, compounds can be included to render the formulation isotonic with the blood of the intended recipient. Compositions containing the compound(s) of the invention can also be prepared in powder or liquid concentrate form.

In one aspect, the liamocins and compositions containing one or more liamocin can be co-administered or co-applied with one or more other therapeutic agents, including other antimicrobial agents and/or pharmaceutically active or veterinarily active agents, such as, but not limited to, geldanamycin, herbimycin, carbacephem, loracarbef, ertapenem, doripenem, imipenem/cilastatin, meropenem, cefadroxil, cefazolin, cefalotin, cefalothin, cefalexin, cefaclor, cefamandole, cefoxitin, cefprozil, cefuroxime, cefixime, cefdinir, cefditoren, cefoperazone, cefotaxime, cefpodoxime, ceftazidime, ceftibuten, ceftizoxime, ceftriaxone, cefepime, ceftobiprole, teicoplanin, vancomycin, macrolides, azithromycin, clarithromycin, dirithromycin, erythromycin, roxithromycin, troleandomycin, telithromycin, spectinomycin, aztreonam, amoxicillin, ampicillin, azlocillin, carbenicillin, cloxacillin, dicloxacillin, flucloxacillin, mezlocillin, meticillin, nafcillin, oxacillin, penicillin, piperacillin, ticarcillin, bacitracin, colistin, polymyxin B, quinolones, ciprofloxacin, enoxacin, gatifloxacin, levofloxacin, lomefloxacin, moxifloxacin, norfloxacin, ofloxacin, trovafloxacin, mafenide, prontosil, sulfacetamide, sulfamethizole, sulfanilimide, sulfasalazine, sulfisoxazole, trimethoprim, trimethoprim-sulfamethoxazole (TMP-SMX), demeclocycline, doxycycline, minocycline, oxytetracycline, tetracycline, arsphenamine, chloramphenicol, clindamycin, lincomycin, ethambutol, fosfomycin, fusidic acid, furazolidone, isoniazid, linezolid, metronidazole, mupirocin, nitrofurantoin, platensimycin, pyrazinamide, quinupristin/dalfopristin, rifampin or rifampicin, and/or tinidazole.

The liamocins and/or compositions containing one or more liamocin may be used either alone or in combination with an immunoregulatory agent ("adjuvant"). An adjuvant is a compound or mixture that enhances the animal's immune response.

In various aspects, an appropriate dosage level will generally be approximately 0.01 mg per kg body weight of the animal to approximately 10 g per kg body weight of the animal per day and can be administered in single or multiple doses. In one embodiment, the dosage level can be approximately 0.1 mg/kg/day to approximately 1 g/kg/day; in another embodiment approximately 0.5 mg/kg/day to approximately 500 mg/kg/day. In another embodiment, a suitable dosage level can be approximately 0.01 mg/kg/day to approximately 250 mg/kg/day; or alternatively approximately 0.05 mg/kg/day to approximately 100 mg/kg/day; or alternatively approximately 0.1 mg/kg/day to approximately 50 mg/kg/day. In other embodiments, the dosage can be approximately 0.05 mg/kg/day to approximately 0.5 mg/kg/day; approximately 0.5 mg/kg/day to approximately 5.0 mg/kg/day; or approximately 5.0 mg/kg/day to approximately 50 mg/kg/day. For oral administration, the compounds and compositions can be administered in the form of tablets containing approximately 1.0 mg to 1000 mg of the active ingredient, or alternatively, approximately 1.0 mg, approximately 5.0 mg, approximately 10 mg, approximately 15 mg, approximately 20 mg, approximately 25 mg, approximately 50 mg, approximately 75 mg, approximately 100 mg, approximately 150 mg, approximately 200 mg, approximately 250 mg, approximately 300 mg, approximately 400 mg, approximately 500 mg, approximately 600 mg, approximately 750 mg, approximately 800 mg, approximately 900 mg, or approximately 1000 mg of the active ingredient. The compound can be administered on a regimen of approximately 1 to approximately 4 times per day, or alternatively approximately once or approximately twice per day. This dosing regimen can be adjusted to provide the optimal therapeutic response.

This invention described herein may be administered to bovine, swine, equine, ovine, goats, camels, and any other mammal including humans; birds (including but not limited to chickens, turkeys, quail, ducks, and other domesticated birds); amphibians; reptiles; and fish.

The method of making liamocins containing specific head groups is also provided herein. *A. pullulans* strain CU 43 (NRRL 50380) can be cultured on 5% w/v mannitol and will produce liamocins with 100% D-mannitol head groups (see Table 7). Culturing *A. pullulans* on 5% w/v D-arabitol liamocins will result in production of liamocins with >98% D-arabitol head group. Culturing *A. pullulans* on D-glucitol (also called sorbitol, 5% w/v) results in production of 35% D-glucitol-liamocins plus 65% D-mannitol-liamocins. Moreover, culturing *A. pullulans* on 5% w/v D-xylitol results in production of a mixture of D-xylitol-liamocins (45%), D-arabitol-liamocins (27%) and D-mannitol-liamocins (28%). Also growth on 5% w/v D-galactitol produces 19% D-galactitol-liamocins, 73% D-mannitol-liamocins and 8% D-glucitol liamocins; and growth on 5% w/v D-ribitol produces 18% D-ribitol liamocins; 63% D-arabitol-liamocins, and 19% D-mannitol-liamocins. Culturing *A. pullulans* on 5% w/v meso-erythritol produces 5% D/L-erythritol-liamocins and 95% D-mannitol-liamocins. Similiarly, culturing *A. pullulans* on 5% w/v D-threitol results in a majority of D-mannitol liamocin (>95%) and a minority of threitol liamocin (<5%) produced. However, culturing *A. pullulans* on 5% w/v L-threitol results in a majority of threitol liamocin (about 75%) and a minority of D-mannitol liamocin (about 25%) produced. The diversity of liamocins produced when grown on different polyols is presented in Table 7. The same polyol head group diversity is also observed for the liamocins from strain RSU 12 (NRRL 50381) when grown on different polyols, and it is anticipated that this would be the case for all liamocin-producing *Aureobasidium pullulans* strains.

In one embodiment, D- and/or L-mannitol liamocin A1, D- and/or L-mannitol liamocin A2, D- and/or L-mannitol liamocin B1, D- and/or L-mannitol liamocin B2, D- and/or L-mannitol liamocin C1, or D- and/or L-mannitol liamocin C2, or a combination thereof, can be used as the antibacterial compound of this invention. In another embodiment, D- and/or L-arabitol liamocin A1, D- and/or L-arabitol liamocin A2, D- and/or L-arabitol liamocin B1, D- and/or L-arabitol liamocin B2, D- and/or L-arabitol liamocin C1, or D- and/or L-arabitol liamocin C2, or a combination thereof, can be used as the antibacterial compound of this invention. In third embodiment, 2-amino-D-mannitol liamocin A1, 2-amino-D-mannitol liamocin A2, 2-amino-D-mannitol liamocin B1, 2-amino-D-mannitol liamocin B2, 2-amino-D-mannitol liamocin C1, or 2-amino-D-mannitol liamocin C2, or a combination thereof, can be used as the antibacterial compound of this invention. In a fourth embodiment, 2-N-acetylamino-D-mannitol liamocin A1, 2-N-acetylamino-D-mannitol liamocin A2, 2-N-acetylamino-D-mannitol liamocin B1, 2-N-acetylamino-D-mannitol liamocin B2, 2-N-acetylamino-D-mannitol liamocin C1, or 2-N-acetylamino-D-mannitol liamocin C2, or a combination thereof, can be used as the antibacterial compound of this invention. In a fifth embodiment, D-fucitol liamocin A1, D-fucitol liamocin A2, D-fucitol liamocin B1, D-fucitol liamocin B2, D-fucitol liamocin C1, or D-fucitol liamocin C2, or a combination thereof can be used as the antibacterial compound of this invention. In a sixth embodiment, L-rhamnitol liamocin A1, L-rhamnitol liamocin A2, L-rhamnitol liamocin B1, L-rhamnitol liamocin B2, L-rhamnitol liamocin C1, L-rhamnitol liamocin C2, or a combination thereof can be used as the antibacterial compound of this invention. In a seventh embodiment, L-glycerol liamocin A1, L-glycerol liamocin A2, L-glycerol liamocin B1, L-glycerol liamocin B2, L-glycerol liamocin C1, L-glycerol liamocin C2, D-glycerol liamocin A1, D-glycerol liamocin A2, D-glycerol liamocin B1, D-glycerol liamocin B2, D-glycerol liamocin C1, D-glycerol liamocin C2, L-threitol liamocin A1, L-threitol liamocin A2, L-threitol liamocin B1, L-threitol liamocin B2, L-threitol liamocin C1, L-threitol liamocin C2, D-threitol liamocin A1, D-threitol liamocin A2, D-threitol liamocin B1, D-threitol liamocin B2, D-threitol liamocin C2, L-erythritol liamocin A1, L-erythritol liamocin A2, L-erythritol liamocin B1, L-erythritol liamocin B2, L-erythritol liamocin C1, L-erythritol liamocin C2, D-erythritol liamocin A1, D-erythritol liamocin A1, D-erythritol liamocin B1, D-erythritol liamocin B2, D-erythritol liamocin C1, D-erythritol liamocin C2, or a combination thereof can be used as the antibacterial compound of this invention. In an eighth embodiment, any combination of any of the compounds (glycerol-liamocins, threitol-liamoicins, erythritol-liamocins, mannitol-liamocins, arabitol-liamocins, 2-amino-D-mannitol liamocins, 2-N-acetylamino-D-mannitol liamocins, D-fucitol liamocins, and L-rhamnitol liamocins) mentioned in this paragraph can be used as the antibacterial compounds for this invention. In another embodiment, any of the compounds described in Formula 1 where $R_1$ is either, independently, $COCH_3$ or H; and $R_2$ is, independently, between two to ten O-linked 3,5-dihydroxydecanoate; and $R_3$ is, independently, one of the following: L- or D-glycerol, L- or D-threitol, L- or D-erythritol, L- or D-arabitol, L- or D-xylitol, L- or D-lyxitol, L- or D-ribitol, L- or D-allitol, L- or D-altritol, L- or D-mannitol, L- or D-iditol, L- or D-gulitol, L- or D-glucitol (also called sorbitol), L- or D-galactitol (also called dulcitol), L- or D-talitol, 2-amino-D-mannitol, 2N-acetylamino-D-mannitol, L-rhamnitol, or D-fucitol; individually or in combination with each other, can be used as the antibacterial compounds for this invention.

Having described the invention in general, below are examples illustrating the generation and efficacy of the invention.

Example 1 Initial Examination of *A. pullulans* Oil's Bactericidal Activity

Several *A. pullulans* strains were isolated from various habitats (e.g., leaves, painted wall surfaces and wood surfaces) and locations in Thailand using half strength corn meal agar (Difco Laboratories, Detroit, Mich.) containing 0.01% (w/v) Rose Bengal (Fischer Scientific, Pittsburgh, Pa.) between August 2005 and May 2006 (see, Manitchotpisit, et al., *Mycological Res.* 113(10):1107-1120 (2009); and Prasongsuk, et al., *World Journal of Microbiology and Biotechnology* 21: 393-398 (2005)). *A. pullulans* strain CU 43 (NRRL 50380) was isolated from a leaf of *Cassia fistula* L. (golden shower tree) in Udonthani, Thailand, in April 2006 and was deposited in ARS Patent Culture Collection, Peoria, Ill. with accession number NRRL 50380 (Manitchotpisit, et al., *Biotechnol. Lett.,* 33(6):1151-7 (2011)). Based on sequence analysis, *A. pullulans* strain CU 43 (NRRL 50380) is in phylogenetic clade 8. Its culture color is yellow, and the oil it produces is yellow and fluorescent. *A. pullulans* strain CU 43 (NRRL 50380) produces approximately 1.9+/−0.9 g/L when cultured under the conditions described infra. See, also, Manitchotpisit, et al. (2011). Other characteristics of *A. pullulans* strain CU 43 (NRRL 50380) is described infra. *A. pullulans* strain RSU 29 (NRRL 50384) was isolated from a *Mangifera indica* L. (mango) leaf in Bangkok, Thailand, in February 2010 and was deposited in ARS Patent Culture Collection, Peoria, Ill. with accession number NRRL 50384. *A. pullulans* strain RSU 29 (NRRL 50384) is in phylogenetic clade 11 and produces high amounts of poly(β-L-malic acid), approximately 11+/−0.9 g/L when cultured under conditions described in Manitchotpisit, et al., *J. Ind. Micro. and Biotechnol.* 39(1):125-132 (2012). Other characteristics of *A. pullulans* strain RSU 29 (NRRL 50384) are described infra. *A. pullulans* strain RSU 32 (NRRL 50382) was isolated as described above from a leaf of a tree in Bangkok, Thailand in February 2010 and was deposited in ARS Patent Culture Collection, Peoria, Ill. with accession number NRRL 50382. *A. pullulans* strain RSU 32 (NRRL 50382) is in phylogenetic clade 8. *A. pullulans* strain RSU 32 (NRRL 50382) produces 9.7+/−0.5 g/L poly(β-L-malic acid). See, Manitchotpisit, et al. (2012). *A. pullulans* strain RSU 12 (NRRL 50381) was isolated from a leaf in Chiyaphum, Thailand, in January 2010 and was deposited in the ARS Patent Culture Collection with accession number NRRL 50381 on Jun. 1, 2010. *A. pullulans* strain RSU 12 (NRRL 50381) is a member of phylogenetic clade 5 and produces relatively high levels of laccase activity (43+/−1.3 mU/mL) under conditions described by Rich et al., *Enzyme and Microbial Technology* 53:33-37 (2013). *A. pullulans* strain RSU 6 (NRRL 50383) was isolated from a leaf in Reykjavik, Iceland, in October 2010 and was deposited in the ARS Patent Culture Collection with accession number NRRL 50383 on Jun. 1, 2010. It is a member of phylogenetic clade 13 and produces relatively high amounts of poly(β-L-malic acid), approximately 11+/−0.0 g/L when cultured under conditions described by Manitchotpisit et al., *J. Ind. Microbiol. Biotechnol.* 39:125-132 (2012).

*A. pullulans* strain RSU 29 (NRRL 50384) also produces pullulan at approximately 9.4+/−0.9 g/L when cultured in 100 ml of pullulan production medium containing 5% (w/v) sucrose, 0.06% (w/v) peptone, 0.04% (w/v) yeast extract, 0.5% (w/v) $K_2HPO_4$, 0.04% (w/v) $MgSO_4.7H_2O$, and 0.1% (w/v) NaCl at 28° C., in 300 ml flasks at 150 rpm shaking for 7 days (Prasongsuk, et al., *J. Ind. Micro. Biotechol.* 34:55-61 (2007)). Pullulan in the supernatant is precipitated using two volumes of 95% ethyl alcohol and dried at 60° C. See, Manitchotpisit, et al., *Mycological Research* 113:1107-1120 (2009).

A number of other *A. pullulans* samples were previously isolated in Thailand using protocols similar to those described supra (Manitchotpisit, et al. (2009), and Prasongsuk, et al. (2005)). These other *A. pullulans* strains were deposited in the ARS Culture Collection, Peoria, Ill. and examples of these strains include those having accession numbers NRRL 62031, NRRL 62034, NRRL 62038, NRRL 62039, NRRL 62040, NRRL 62041, and NRRL 62042.

The *A. pullulans* strains described herein are maintained on yeast malt extract agar (YMA). For assessment of oil production, 50 ml cultures in 250 ml flasks are grown in 5% (w/v) sucrose, 0.06% (w/v) peptone, 0.04% (w/v) yeast extract, 0.5% (w/v) $K_2HPO_4$, 0.04% (w/v) $MgSO_4.7H_2O$, and 0.1% (w/v) NaCl for 7 days at 28° C. with shaking at 150 rpm (see Manitchotpisit, et al. (2011)).

Mannitol-liamocin-containing oil is extracted by a modification of the method of Kurosawa, et al. (1994). Cells and heavy oil are removed by centrifugation at 5,000×g for 10 minutes. Extracellular heavy oil appears as a layer beneath the precipitated cells. Cells are gently resuspended in 3-5 ml of distilled water and transferred to a screw-cap glass tube (13 mm×100 mm). Culture flasks and centrifuge bottles are washed with between 3 ml and 5 ml of methyl ethyl ketone; the heavy oil is dissolved in methyl ethyl ketone. The dissolved oil is recombined with the resuspended cells, and the mixture is vortexed vigorously and allowed to separate overnight at room temperature. The aqueous and extracted cell layers are then removed, and the solvent is evaporated from the oil overnight under a stream of air. Oil yields are expressed as dry weights. Surprisingly, *A. pullulans* strain RSU 29 (NRRL 50384) produces oil at approximately 8.4+/−0.8 g/L. The oil produced by *A. pullulans* strain RSU 29 (NRRL 50384) is olivaceous in color.

The eight bacterial strains listed in Table 1 are used in the antibacterial activity assays. *Streptococcus agalactiae* and *S. uberis* (gifts from D. Donovan, ARS, USDA, Beltsville, Md.), *Lactobacillus fermentum* laboratory strain number 0315-1 (Bischoff, et al., *Biotechnology and Bioengineering* 103:117-122 (2009)), *Enterococcus faecalis* (ATCC Accession Number 29212), *Bacillus subtilis* MW10 (*Bacillus* Genetic Stock Center Accession Number 1A751), *Staphylococcus aureus* (ATCC Accession Number 29213), *Escherichia coli* (ATCC Accession Number 25922), and *Pseudomonas aeruginosa* (ATCC Accession Number 27853) are obtained from the indicated source. *S. uberis*, *S. agalactiae*, *S. aureus*, *E. coli*, and *P. aeruginosa* are cultured in tryptic soy broth (TSB) at 37° C. TSB contains the following: peptone from casein 17.0 g/L; peptone from soymeal 3.0 g/L; D(+)glucose 2.5 g/L; sodium chloride 5.0 g/L; and di-potassium hydrogen phosphate 2.5 g/L. *E. faecalis* are cultured in Bacto Brain Heart Infusion broth (BHI) (Becton Dickenson, Franklin Lakes, N.J.) at 37° C. *L. fermentum* are cultured in MRS broth at 37° C. MRS broth contains the following: peptone from casein 10.0 g/L; meat extract 8.0 g/L; yeast extract 4.0 g/L; D(+)-glucose 20.0 g/L; di-potassium hydrogen phosphate 2.0 g/L; Tween® 80 1.0 g/L; di-ammonium hydrogen citrate 2.0 g/L; sodium acetate 5.0 g/L; magnesium sulfate 0.2 g/L; and manganese sulfate 0.04 g/L.

Minimum inhibitory concentrations (MICs) are determined according to the broth microdilution method described in National Committee for Clinical Laboratory Standards approved standard M31-A (1999) with *A. pullulans* strain CU 43 (NRRL 50380) mannitol-liamocin-containing oil concentrations ranging from 20 µg/ml to 1250 µg/ml. The results are contained in Table 1.

TABLE 1

| Bacteria | Minimum Inhibitory Concentration[a] (µg/ml) |
|---|---|
| *Streptococcus agalactiae* | 39 |
| *Streptococcus uberis* | 78 |
| *Enterococcus faecalis* | 312 |
| *Bacillus subtilis* | 640 |
| *Staphylococcus aureus* | >1250 |
| *Lactobacillus fermentum* | >1250 |
| *Escherichia coli* | >1250 |
| *Pseudomonas aeruginosa* | >1250 |

[a]MICs are determined by broth dilution method with concentrations ranging from 20 µg/ml to 1250 µg/ml In addition to the MICs of *A. pullulans* strain CU 43 (NRRL 50380) in Table 1, mannitol-liamocin-containing oils from the following nine *A. pullulans* strains are obtained using the protocol described supra and also are tested for antibacterial activity: ARS Culture Collection Accession Numbers NRRL 62031, NRRL 62034, NRRL 62038, NRRL 62039, NRRL 62040, NRRL 62041, NRRL 62042, *A. pullulans* strain RSU 32 (NRRL 50382), and *A. pullulans* strain RSU 29 (NRRL 50384). Oils from these other *A. pullulans* isolates all produce results similar to those observed for the oil obtained from *A. pullulans* strain CU 43 (NRRL 50380) shown in Table 1.

The purified oil, which contains mannitol-liamocins, from *A. pullulans* strain CU 43 (NRRL 50380) are bactericidal for *S. agalactiae*, reducing viable bacterial densities 1.4 log (CFU/ml) within 1 hour at a concentration as low as 250 µg/ml (see Table 2). The mannitol-liamocin-containing oil is diluted to the indicated concentration in phosphate buffered saline containing approximately $10^7$ CFU/ml of *S. agalactiae*. Following 1 hour incubation at room temperature, samples are spread on TSB agar plates for enumeration of bacteria. Data are reported as the bacterial density of the surviving bacteria following mannitol-liamocins oil treatment.

TABLE 2

| Liamocins concentration (μg/ml) | CFU/ml |
|---|---|
| 0 | $1.14 \times 10^7$ |
| 16 | $9.07 \times 10^6$ |
| 31 | $4.69 \times 10^6$ |
| 62 | $1.05 \times 10^6$ |
| 125 | $7.58 \times 10^5$ |
| 250 | $4.40 \times 10^5$ |
| 500 | $4.23 \times 10^5$ |
| 1000 | $4.42 \times 10^5$ |

Example 2 *Streptococcus* Spp. Susceptibility to *A. pullulans* Oil

*S. agalactiae* (gift from D. Donovan, ARS, USDA, Beltsville, Md.), *S. agalactiae* ARS Culture Collection Accession Number NRRL B-1815, *S. uberis* (gift from D. Donovan, ARS, USDA, Beltsville, Md.), *S. mitis* ARS Culture Collection Accession Number NRRL B-14574, *S. infantarius* ARS Culture Collection Accession Number NRRL B-41208, *S. mutans* (ATCC Accession Number 25175), *S. pneumoniae* (ATCC Accession Number 55143), *S. salivarius* (Accession No. NRRL B-3714), *S. suis* (Accession No. ATCC 43765), and *S. sobrinus* ARS Culture Collection Accession Number NRRL B-4468 are grown using the protocol of Example 1 and undergo MIC assays using unpurified mannitol-liamocin containing oil obtained from *A. pullulans* strain CU 43 (NRRL 50380) using the protocol described in Example 1 above. MICs are determined by broth dilution method, with serial two-fold dilutions of *A. pullulans* mannitol-liamocin-containing oil ranging from 10 μg/ml to 1250 μg/ml. See Table 3.

TABLE 3

| *Streptococcus* species | Minimum Inhibitory Concentration (μg/ml) |
|---|---|
| *S. agalactiae* | 39 |
| *S. agalactiae* (Accession No. NRRL B-1815) | 20 |
| *S. infantarius* (Accession No. NRRL B-41208) | 78 |
| *S. mitis* (Accession No. NRRL B-14574) | 20 |
| *S. mutans* (ATCC Accession Number 25175) | 78 |
| *S. pneumoniae* (Accession No. ATCC 55143) | ≤10 |
| *S. salivarius* (Accession No. NRRL B-3714) | ≤10 |
| *S. sobrinus* (Accession No. NRRL B-4468) | >1250 |
| *S. suis* (Accession No. ATCC 43765) | ≤10 |
| *S. uberis* | 78 |

Next, the antibacterial activity of *A. pullulans* mannitol-liamocin-containing oil is assayed for heat stability. The oil from each of *A. pullulans* deposited in ARS Culture Collection Accession Numbers NRRL 62031, NRRL 62034, NRRL 62038, NRRL 62039, NRRL 62040, NRRL 62041, and *A. pullulans* strain CU 43 (NRRL 50380) is obtained using the protocol in Example 1 and diluted to 1250 μg/ml in culture media, and heated in an autoclave (121° C., 15 minutes). MICs for *Streptococcus agalactiae* is determined by broth dilution susceptibility testing as described above. See Table 4. Autoclaving had no effect on the MIC of the oil.

TABLE 4

| *Aureobasidium pullulans* strains | MIC (μg/ml) | MIC (μg/ml) (autoclaved oil) |
|---|---|---|
| Accession No. NRRL 50380 | 39 | 39 |
| Accession No. NRRL 62031 | 39 | 39 |
| Accession No. NRRL 62034 | 78 | 39 |
| Accession No. NRRL 62038 | 78 | 78 |
| Accession No. NRRL 62039 | 39 | 39 |
| Accession No. NRRL 62040 | 39 | 39 |
| Accession No. NRRL 62041 | 39 | 39 |

Example 3 Viability of *S. agalactiae* NRRL B-1815 Following 1 Hour Exposure to Oil Containing Mannitol-Liamocins Viability of *S. agalactiae* following exposure to oil containing mannitol-liamocins is determined by a commercial two-color fluorescence assay (LIVE/DEAD BacLight Bacterial Viability Assay, Molecular Probes, Inc., Eugene, Oreg.) as well as by enumeration of surviving cells on agar media. *S. agalactiae* is grown according to the protocol of Example 1, and is chosen for this assay because it is an important agricultural pathogen, causing mastitis in cattle. Mid-log phase bacteria are suspended in sterile saline to an optical density of 0.6 at 600 nm. Oil from *A. pullulans* CU 43 (NRRL 50380) is obtained using the protocol in Example 1, and bacterial cells are treated with varying concentrations of mannitol-liamocin oil for 1 hour at room temperature. For the fluorescence assay, cells are stained with SYTO 9 and propidium iodide, and fluorescence intensities at 530 nm (green) and 630 nm (red) are measured with an excitation wavelength of 485 nm. As specified by the manufacturer, a standard curve plotting the ratio of green:red fluorescence intensities versus percent live cells is constructed by staining bacterial suspensions of varying concentrations of saline-treated cells (live) and isopropanol-treated cells (dead). See FIG. 2B. For enumeration of surviving bacteria, dilutions of treated cells are spread on tryptic soy broth agar plates and incubated at 37° C.

Figure 2A:
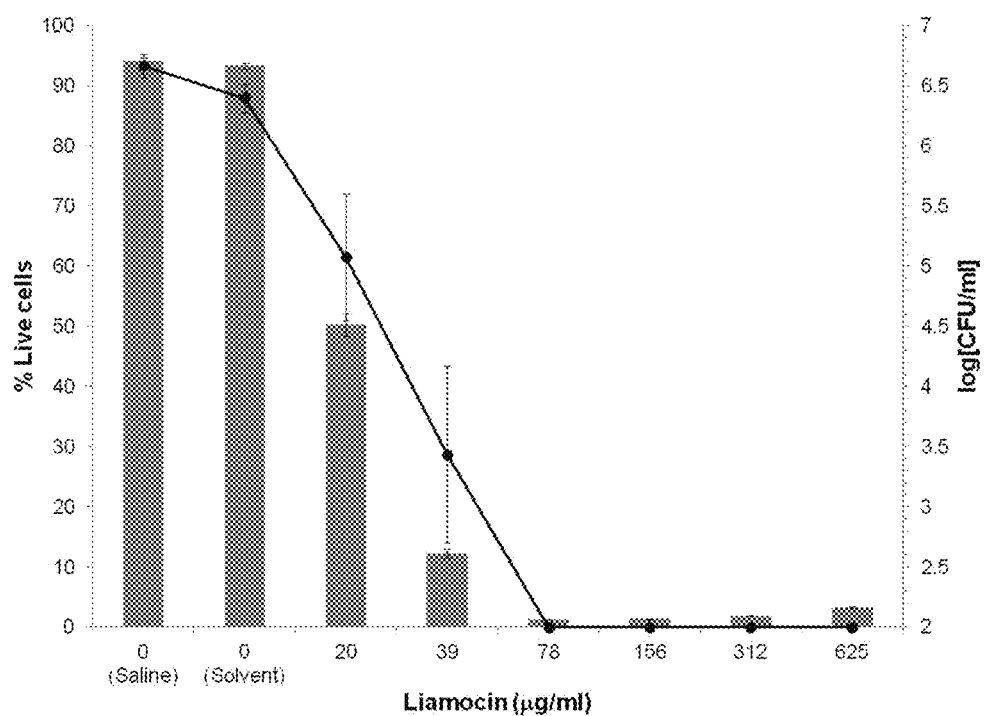
FIG. 2A shows the viability of *S. agalactiae* following exposure to the indicated concentration of mannitol-containing liamocin oil obtained from *A. pullulans* NRRL 50380. The bacterial viability is determined by a two-color fluorescence assay and by enumeration of surviving cells. Controls (0 µg/ml mannitol-liamocin containing oil) include bacterial cells treated with saline and bacterial cells treated with 2-butanone:DMSO solvent (1.25% (v/v)). All assays are performed in triplicate. Bars indicate the percentage of live cells determined using the LIVE/DEAD BacLight Bacterial Viability Assay and using a standard curve plotting percent live cells versus the green:red fluorescence ratio (FIG. 2B). The line indicates the bacterial density (log [CFU/ml]) of the surviving *Streptococcus* following 1 hour exposure to the indicated concentration of liamocin.
Figure 2B:
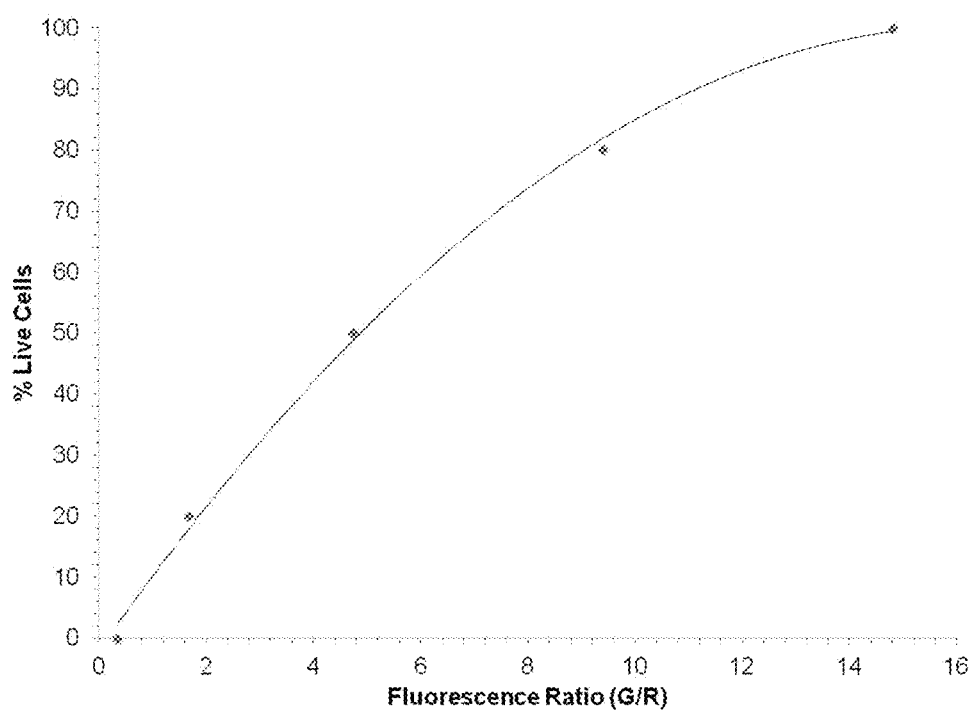
FIG. 2B shows the standard curve plotting percent live cells versus the green:red fluorescence ratio using the LIVE/DEAD BacLight Bacterial Viability Assay.

Treatment of *S. agalactiae* NRRL B-1815 with 20 μg/ml and 39 μg/ml mannitol-liamocin containing oil reduces the percentage of live cells to 50% and 12%, respectively (FIG. 2A). Values of percent live cells for the saline-treated and 2-butanone:DMSO-treated controls are not significantly different (p>0.05). Similarly, exposure to 39 μg/ml mannitol-liamocin oil reduces viable colony forming units (CFUs) three log-fold compared to 2-butanone:DMSO-treated cells (3.4 $\log_{10}$ CFU/ml and 6.4 $\log_{10}$ CFU/ml, respectively; FIG. 2A). Higher concentrations reduce viability below 2 $\log_{10}$ CFU/ml. The fluorescence assay is based on the differential labeling of cells with intact and damaged membranes, i.e. the propidium iodide stain only penetrates cells with damaged membranes. The sudden decrease in the green:red fluorescence ratio following treatment with mannitol-liamocin containing oil suggests a rapid loss of membrane integrity. Taken with the corresponding decrease in recovery of viable cells on TSB agar plates following exposure, the mannitol-liamocins appear to be bactericidal for *S. agalactiae*.

Figure 3:
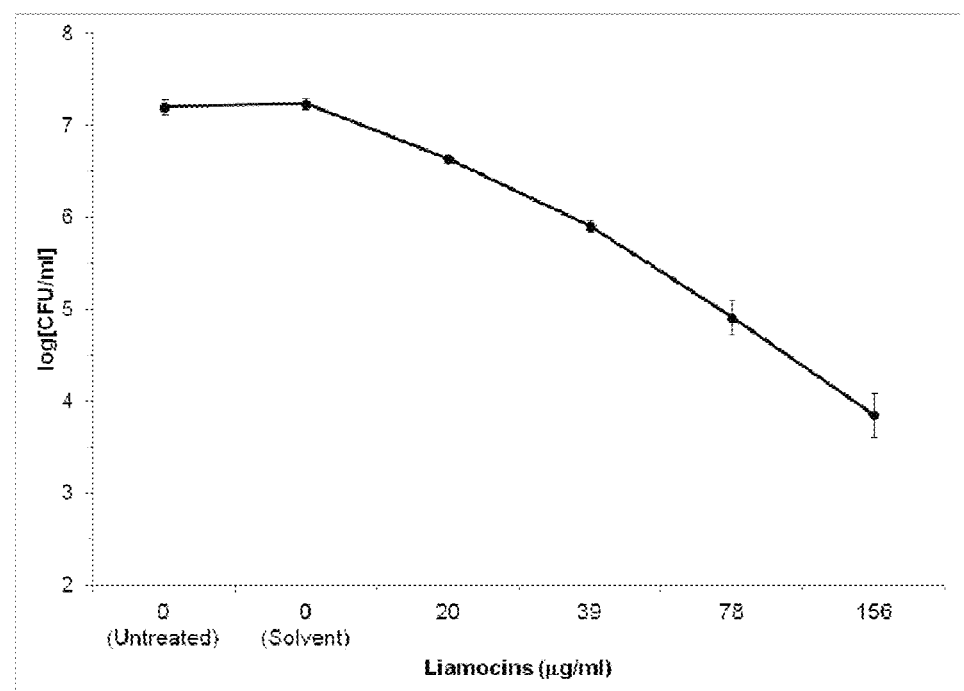
FIG. 3 shows the viability of *S. uberis* following exposure to varying concentrations of mannitol-liamocin containing oil obtained from *A. pullulans* NRRL 50380 as well as two negative controls (saline and 2-butanone:DMSO solvent (1.25% (v/v)).

Example 4 Viability of *S. uberis* Following 1 Hour Exposure to Mannitol-Liamocins Viability of *S. uberis* following exposure to liamocins is determined by enumeration of surviving cells on agar media. Mannitol-liamocin oil from *A. pullulans* NRRL 50380 is obtained using the protocol in Example 1 and prepared per the protocol of Example 3. *S. uberis* is grown according to the protocol of Example 1. Mid-log phase bacteria are suspended in sterile saline to an optical density of 0.6 at 600 nm. *S. uberis* cells are treated with 0, 20, 39, 78, or 156 µg/ml of mannitol-liamocin oil from *A. pullulans* NRRL 50380 for 1 hour at room temperature, and dilutions of treated *S. uberis* cells are spread on tryptic soy broth agar plates and incubated at 37° C. *S. uberis* are treated with two negative controls: saline and 2-butanone:DMSO solvent (1.25% (v/v)). Bacterial viability following exposure to the indicated concentration of mannitol-liamocin oils from *A. pullulans* NRRL 50380 is determined by enumeration of surviving bacterial cells. Treatment of *S. uberis* with 156 µg/ml reduces the viability over 3 log(CFU/ml) in one hour (see FIG. 3). Assays are performed in duplicate.

Example 5 Bactericidal Activity for Individual Mannitol-Liamocin Components of *A. pullulans* Oil

Figure 4:
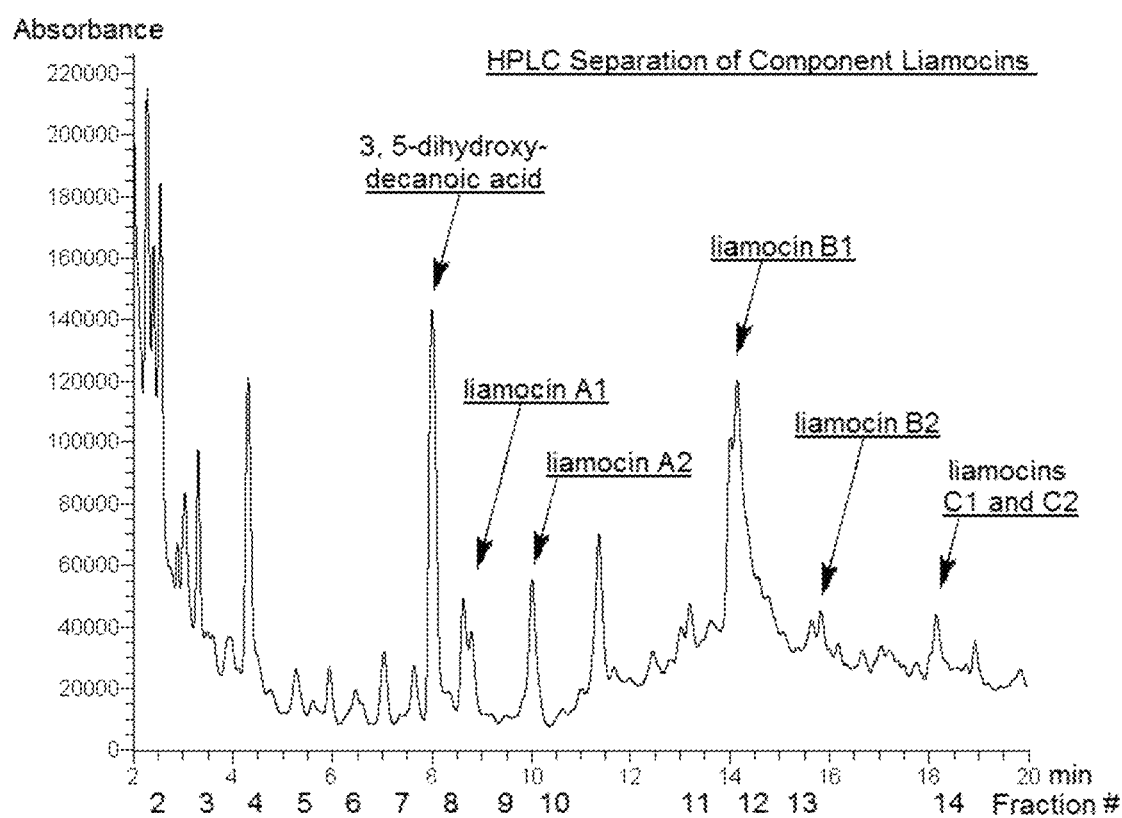
FIG. 4 shows the peaks and fractions of reverse phase HPLC purification of the liamocin-containing oil produced by *A. pullulans*.

*A. pullulans* strain CU 43 (NRRL 50380) is cultured as described in Example 1 supra. As described in Price, et al. (2013), the produced oil contains at least six different mannitol-liamocin components (mannitol-liamocin A1, mannitol-liamocin A2, mannitol-liamocin B1, mannitol-liamocin B2, mannitol-liamocin C1, and mannitol-liamocin C2). Mannitol-liamocin A1, mannitol-liamocin A2, mannitol-liamocin B1, mannitol-liamocin B2, mannitol-liamocin C1, and mannitol-liamocin C2 are individually isolated and purified by the following protocol for reverse phase HPLC. The Surveyor HPLC (ThermoFisher Scientific, Waltham, Mass.) with a photoarray detector attached is used to fractionate the oil from *Aurobasidium pullulans* NRRL 50380 using a Brownlee Spheri 5 RP18 HPLC column (PerkinElmer, Inc., Waltham, Mass.) using a linear gradient of 50-100% acetonitrile in water (1 ml/min). See FIG. 4.

Figure 5:
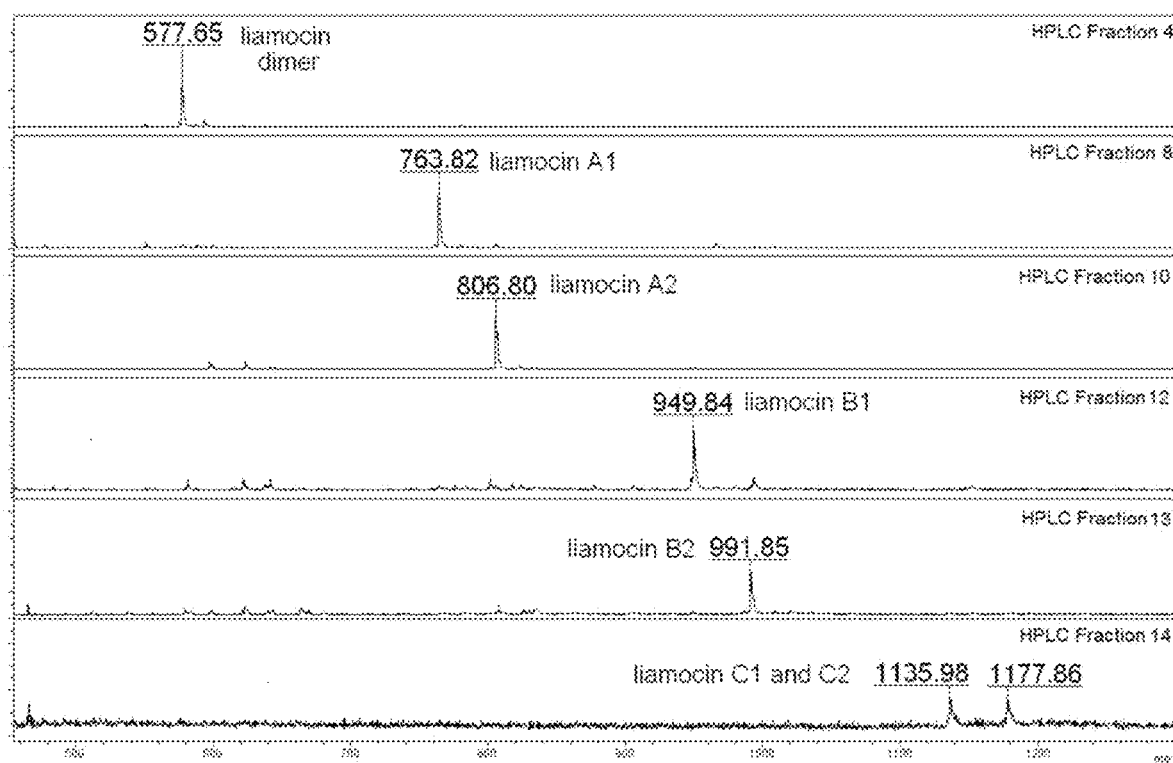
FIG. 5 shows the MALDI-MS characterizations of the HPLC-purified liamocin components of the liamocin-containing oil produced by *A. pullulans*.

Fractions collected from the HPLC run are pooled and undergo matrix-assisted laser desorption/ionization mass spectrometry (MALDI-MS) on a Bruker-Daltonic Microflex mass spectrometer (Bruker Corp., Billerica, Mass.) giving molecular $[M+Na]^+$ adduct ions in the mass range 500-1200 Da (mannitol-liamocin dimers, (m/z 577.65); trimers mannitol-A1 (m/z 763.82) and mannitol-A2 (m/z 806.80); tetramers mannitol-B1 (m/z 949.84) and mannitol-B2 (m/z 991.85); and pentamers mannitol-C1 (m/z 1135.98) and mannitol-C2 (m/z 1177.86)). The MALDI-MS matrix is saturated 2,5-dihydrobenzoic acid in acetonitrile, and uses a pulsed $N_2$ laser, emitting at 337 nm. Ion source 1 (IS 1) is set at 19.0 kV, and source 2 (IS 2) is set at 15.9 kV (83.7% of IS 1), with lens and reflector voltages of 9.79 and 19.99 kV, respectively. See FIG. 5 for results.

Antibacterial activity for each fraction of the HPLC is measured qualitatively by disc diffusion assay. *S. agalactiae* at a density of 0.5 McFarland units are diluted 1:100 in PBS, and 20 µl are evenly spread on TSB agar media. Paper discs (6 mm diameter) are placed on surface. HPLC fractionated oils are dissolved to a concentration of 5 mg/ml in solvent (1:1 dimethylsulfoxide:2-butanone), and samples (10 µl) are applied to each disc. Plates are incubated at 37° C. overnight, and scored for a growth inhibition zone surrounding the disc, which indicates antibacterial activity. 5 mg/ml of purified oil is used as positive control, and acetonitrile solvent for HPLC is used as negative control. Fractions 8 (mannitol-liamocin A1), 9 (mannitol-liamocin A2) 10 (mannitol-liamocin A2), 11 (mannitol-liamocin B1), 12 (mannitol-liamocin B1), 13 (mannitol-liamocin B2), and 14 (mannitol-liamocin C1 and mannitol-liamocin C2 combined) exhibit bactericidal activity against *S. agalactiae*.

Fractions 5-14 that were obtained from the HPLC fractionation (above) are assayed for antibacterial activity against *S. agalactiae* by the broth dilution method with serial two-fold dilutions of each component ranging from approximately 128 µg/ml to approximately 2 µg/ml. The primary component and minimum inhibitory concentration of each fraction assayed is provided in Table 5. Fraction 12, containing mannitol-liamocin B1 had the lowest minimum inhibitory concentration (i.e. highest antibacterial activity) of the fractions.

TABLE 5

| Fraction | Component(s) | Minimum Inhibitory Concentration (µg/ml) |
|---|---|---|
| 5 | | >128 |
| 6 | | >128 |
| 7 | mannitol-liamocin A1 | >128 |
| 8 | mannitol-liamocin A1 | 64 |
| 9 | mannitol-liamocin A2 | 128 |
| 10 | mannitol-liamocin A2 | 64 |
| 11 | mannitol-liamocin B1 | 64 |
| 12 | mannitol-liamocin B1 | 16 |
| 13 | mannitol-liamocin B2 | 128 |
| 14 | mannitol-liamocin C1 and mannitol-liamocin C2 | 32 |

Example 6 Teat Dip Containing Mannitol-Liamocin-Containing Oil Reduces *Streptococcus agalactiae* Associated with Bovine Mastitis Three different teat dip solutions containing 2% v/v glycerin and *A. pullulans* mannitol-liamocin-containing oil at either approximately 0.01% v/v, approximately 0.1% v/v, or approximately 10% v/v, are made. Thirty-two teats of eight lactating Holstein cows are used for teat dip trials. *S. agalactiae* is grown on tryptic soy agar (BD Diagnostics, Sparks, Md.) at 37° C. for 18 to 24 hours, and colonies are resuspended in phosphate buffered saline to a turbidity of 0.5 McFarland (approximately 8 log(CFU/ml). A 7 log(CFU/ml) challenge culture of *S. agalactiae* is prepared by diluting the 0.5 McFarland suspension ten-fold in tryptic soy broth (BD Diagnostics, Sparks, Md.). The challenge and teat dipping procedure is a modification of that described by Klosterman and coworkers (Klosterman et al., *J. Dairy Res.* 77:231-238 (2010)). Teats and udder are washed with lukewarm water and disinfected twice with 70% v/v isopropanol. Each disinfected teat is dipped once in a 25 ml beaker containing 12 ml of *S. agalactiae* challenge culture. Following a 5 minute drainage time, each teat is submerged for 10 minutes in 20 ml of the selected mannitol-liamocin-containing oil teat dip solution or a control solution (2% v/v glycerin). For each cow, one teat is dipped in the control solution, one teat in 0.01% v/v mannitol-liamocin-containing oil teat dip solution, one in 0.1% v/v mannitol-liamocin-containing oil teat dip solution, and one in the 10% v/v mannitol-liamocin-containing oil teat dip solution. Surviving bacteria are recovered by submerging each teat into sterile beakers containing 20 ml of Oxoid Maximum Recovery Diluent (Thermo Scientific, Waltham, Mass.). Surviving bacteria are enumerated by plating appropriate dilutions on tryptic soy agar and incubating at 37° C. for 18 to 24 hours. The average CFU/ml for each mannitol-liamocin-containing oil treatment group is compared with the average for the control group, and a Student's t-test is used to evaluate statistical differences between control and mannitol-liamocin-containing oil treatment groups.

Example 7 Mouthwash Containing Mannitol-Liamocin-Containing Oil or Mannitol-Liamocin A1, Mannitol-Liamocin A2, Mannitol-Liamocin B1 or Mannitol-Liamocin B2 Reduces *S. mutans* Population in Humans Four different mouthwash solutions containing menthol 0.042% v/v, thymol 0.064% v/v, methyl salicylate 0.06% v/v, eucalyptol 0.092% v/v, ethanol 40% v/v, and *A. pullulans* mannitol-liamocin-containing oil in either approximately 0.01% v/v, approximately 0.1% v/v, approximately 1% v/v or approximately 10% v/v, are made. Six groups of five subjects each (one group is negative control (water) and another group uses Listerine®) undergo mouth swabs prior to initiation of study, and at 7, 14, and 21 days. Concentrations of *S. mutans* are determined by enumeration on selective media as described by Wan and coworkers (Wan, et al. *Australian Dental Journal* 47:21-26 (2002)). Each swab is placed in two ml of phosphate buffered saline and vortexed for 5 minutes. Serial 10-fold dilutions are streaked on TYCSB plates, cultured at 37° C. for three days, and scored for bacterial colonies. TYCSB media contains the following per liter: 0.2 g L-cystine HCl monohydrate; 15 g bacto peptone; 5 g yeast extract; 0.1 g $Na_2SO_3$; 0.1 g NaCl; 1.0 g $Na_2HPO_4.7H_2O$; 2.0 g $NaHCO_3$; 20 g $C_2H_3O_2Na_3H_2O$; 20% w/v sucrose; 15 g granulated agar; 0.2 U/ml bacitracin; distilled water. Each study participant rinses his/her mouth twice daily with the provided mouthwash (or water for the negative control group). The amount of *S. mutans* in each subject's mouth determined by the culture is combined with each subject with the same group for an average for each mouth swab. The average for each *A. pullulans* oil containing mouthwash group is compared to the average for the negative control group and the average for the positive control group.

Six separate mouthwashes are prepared as described supra, except replacing *A. pullulans* mannitol-liamocin-containing oil with either mannitol-liamocin A1, mannitol-liamocin A2, mannitol-liamocin B1, mannitol-liamocin B2, mannitol-liamocin C1, or mannitol-liamocin C2 at approximately 5% v/v for each mouthwash. Eight groups of five subjects each (one group is negative control (water) and another group uses Listerine®) undergo mouth swabs prior to initiation of study, and at 7, 14, and 21 days. Concentrations of *S. mutans* are determined by enumeration on selective media as described by Wan, et al. (2002). Each swab is placed in two ml of phosphate buffered saline and vortexed for 5 minutes. Serial 10-fold dilutions are streaked on TYCSB plates, cultured at 37° C. for three days, and scored for bacterial colonies. TYCSB media contains the following per liter: 0.2 g L-cystine HCl monohydrate; 15 g bacto peptone; 5 g yeast extract; 0.1 g $Na_2SO_3$; 0.1 g NaCl; 1.0 g $Na_2HPO_4.7H_2O$; 2.0 g $NaHCO_3$; 20 g $C_2H_3O_2Na_3H_2O$; 20% w/v sucrose; 15 g granulated agar; 0.2 U/ml bacitracin; distilled water. Each study participant rinses his/her mouth twice daily with the provided mouthwash (or water for the negative control group). The amount of *S. mutans* in each subject's mouth determined by the culture is combined with each subject with the same group for an average for each mouth swab. The average for each group (mouthwash containing mannitol-liamoncin A1, mannitol-liamocin A2, mannitol-liamocin B1, mannitol-liamcin B2, mannitol-liamocin C1, or mannitol-liamocin C2) is compared to the average for the negative control group and the average for the positive control group.

Example 8 Liamocin with Varying Headgroup

When *A. pullulans* is cultured on different media containing different polyols, the liamocins produced can contain polyol head groups different from mannitol. Arabitol, glycerol, xylitol, glucitol and galactitol are some of the possible polyol head groups of $R_3$ of Formula 1, supra. For example, when *A. pullulans* strain RSU 12 (NRRL 50381) is grown in Doshida medium containing 1% glucose, 0.05% L-asparagine.H2O, 0.05% $K_2HPO_4$; 40 g/L sea salts (Sigma Aldrich, St. Louis, Mo.), at pH 7.0 (see Doshida, et al., *J. Antibiotic* 49(11):1105-1109 (1996)), liamocins with mannitol, glycerol, and arabitol head groups are produced. Table 6, infra, lists the type of liamocin and its percentage produced by different strains of *A. pullulans* when cultured in different media. In Table 6, "Gro-A1" is glycerol-liamocin A1; "Gro-A2" is glycerol-liamocin A2; "Gro-B1" is glycerol-liamocin B1, and "Gro-B2" is glycerol-liamocin B2. Similarly, "Ara-A1" is arabitol-liamocin A1; "Ara-A2" is arabitol liamocin A2; "Ara-B1" is arabitol-liamocin B1; and "Ara-B2" is arabitol liamocin B2. Finally, "Man-A1" is mannitol-liamocin A1; "Man-A2" is mannitol-liamocin A2; "Man-B1" is mannitol-liamocin B1; and "Man-B2" is mannitol-liamocin B2. The media used are Doshida media (see above); Kurosawa media contains 12% glucose; 0.15% $NaNO_3$; 0.10% $KNO_3$; 0.005% $KH_2PO_4$; 0.02% $MgSO_4.7H_2O$; 2.0 ppm $ZnSO_4.7H_2O$; 0.02% yeast extract; at an undefined pH (see, Kurosawa, et al., *Biosci. Biotechnol. Biochem.* 58:2057-2060 (1994)); PM media contains 5% sucrose; 0.06% peptone; 0.04% yeast extract; 0.5% $K_2HPO_4$; 0.04% $MgSO_4.7H_2O$; 0.1% NaCl; at pH 6.5 (see Manitchotpisit, et al., *Biotechnol. Lett.*, 33(6):1151-7 (2011)); and Wang media contains 8.0% glucose; 0.7% $K_2HPO_4$; 0.25% $Na_2PO_4$; 0.15% $MgSO_4.7H_2O$; 0.015% $CaCl_2$; 0.015% $FeCl_3.7H_2O$; 0.002% $ZnSO_4.7H_2O$; 0.002% $MnSO_4.H_2O$; 0.02% $(NH_4)_2SO_4$; 0.02% yeast extract; at pH 6.0 (see Wang, et al., *Process Biochemistry* 49(5):725-731 (2014)). *A. pullulans* strains CU 43 (NRRL 50380), RSU 6 (NRRL 50383), RSU 12 (NRRL 50381), RSU 29 (NRRL 50384), RSU 32 (NRRL 50382), and NBRC 108784 are cultured in these four different media. Liamocins are extracted from whole cultures (100 mL) with methyl ethyl ketone. The methyl ethyl ketone layers are dried down, and re-dissolved in acetonitrile (1 mL). MALDI-TOF mass spectra are acquired using 2,5-dihydrobenzoic acid as matrix, plus saturated aqueous sodium bicarbonate (1 µL) to ensure that the ions obtained are in the sodiated $[M+Na]^+$ form. The relative areas (%) of the ions are quantified using Bruker Daltonics Flexanalysis software. The indicated types and percentages of liamocins produced are provided in Table 6.

TABLE 6

| Strains | Amount of Liamocin Trimers (%) | | | | | | Amount of Liamocin Tetramers (%) | | | | | |
|---|---|---|---|---|---|---|---|---|---|---|---|---|
| | Gro-A1 | Gro-A2 | Ara-A1 | Ara-A2 | Man-A1 | Man-A2 | Gro-B1 | Gro-B2 | Ara-B1 | Ara-B2 | Man-B1 | Man-B2 |
| Doshida medium | | | | | | | | | | | | |
| CU 43 | — | — | 6.9 | 13.1 | 19.0 | 37.3 | — | — | 5.0 | 3.3 | 10.6 | 4.8 |
| RSU 6 | 22.7 | 6.4 | 7.5 | — | 10.0 | 3.8 | 19.8 | — | 13.3 | — | 16.5 | — |
| RSU 12 | 3.2 | — | 25.3 | 20.9 | 21.9 | 13.6 | 1.9 | — | 8.2 | — | 5.0 | — |
| RSU 29 | — | 4.8 | 9.1 | 20.5 | 17.7 | 34.8 | — | — | 5.5 | — | 7.6 | — |
| RSU 32 | — | — | 14.8 | 26.4 | 14.5 | 24.5 | — | — | 10.0 | — | 9.8 | — |
| NBRC 108784 | — | — | 22.0 | 25.5 | 24.1 | 28.4 | — | — | — | — | — | — |
| Kurosawa medium | | | | | | | | | | | | |
| CU 43 | — | — | — | — | 31.0 | 15.0 | — | — | — | — | 45.9 | 8.1 |
| RSU 6 | — | — | 28.5 | — | 34.8 | — | — | — | — | — | 36.7 | — |
| RSU 12 | — | — | 13.0 | 12.8 | 28.2 | 21.5 | — | — | 9.3 | — | 15.2 | — |
| RSU 29 | — | — | — | 6.4 | 28.7 | 52.3 | — | — | — | — | 12.6 | — |
| RSU 32 | — | — | 7.4 | 10.2 | 21.1 | 29.3 | — | — | 8.7 | — | 23.3 | — |
| NBRC 108784 | — | — | 34.6 | 25.1 | 23.5 | 16.8 | — | — | — | — | — | — |
| PM + 5% sucrose medium | | | | | | | | | | | | |
| CU 43 | — | — | — | — | 23.0 | 42.9 | — | — | — | — | 23.3 | 10.8 |
| RSU 6 | — | — | — | — | 46.8 | — | — | — | — | — | 53.2 | — |
| RSU 12 | — | — | 7.8 | 7.1 | 36.6 | 26.1 | — | — | 5.6 | — | 16.8 | — |
| RSU 29 | — | — | — | 4.1 | 24.6 | 56.6 | — | — | — | — | 14.7 | — |
| RSU 32 | — | — | — | 7.3 | 22.2 | 37.8 | — | — | — | — | 19.8 | 12.9 |
| NBRC 108784 | — | — | — | — | 41.8 | 58.2 | — | — | — | — | — | — |
| Wang medium | | | | | | | | | | | | |
| CU 43 | — | — | — | — | 21.9 | 48.7 | — | — | — | — | 24.1 | 5.3 |
| RSU 6 | 11.8 | 4.3 | 5.1 | — | 15.7 | 4.8 | 14.7 | — | 9.1 | — | 34.5 | — |
| RSU 12 | — | — | 10.7 | 12.2 | 29.5 | 29.3 | — | — | 6.5 | — | 11.8 | — |
| RSU 29 | — | — | 6.3 | 11.5 | 25.8 | 41.9 | — | — | 4.1 | — | 10.4 | — |
| RSU 32 | — | — | 5.7 | 13.2 | 16.4 | 39.8 | — | — | 7.3 | — | 17.6 | — |
| NBRC 108784 | — | — | 16.8 | 17.4 | 33.9 | 31.9 | — | — | — | — | — | — |

MALDI-TOF MS analysis is performed on the liamocins from *A. pullulans* strain CU 43 (NRRL 50380) cultured on the four culture media in Table 6. When cultured in PM+5% sucrose medium, Wang medium, and Kurosawa medium, the primary ions observed are for mannitol-liamocin trimers (Man-A1 and Man-A2) and tetramers (Man-B1 and Man-B2), with no MALDI-TOF MS ions for arabitol-liamocins. However, when cultured in Doshida medium, four new liamocins are observed with arabitol head groups (arabitol-liamocin trimers Ara-A1, Ara-A2, plus tetramers Ara-B1 and Ara-B2), in addition to the previously described mannitol-liamocins. MALDI-TOF MS analysis is also performed on the liamocins from *A. pullulans* strain RSU 12 (NRRL 50381) cultured on the four culture media in Table 6. When *A. pullulans* strain RSU 12 (NRRL 50381) is cultured in PM+5% sucrose medium, the major ions are for mannitol-liamocins (Man-A1, Man-A2, and Man-B1) plus ions for arabitol-liamocins (Ara-A1, Ara-A2, and Ara-B1). When grown in Doshida medium other MALDI-TOF MS ions are observed that correspond to glycerol-liamocins (Gro-A1 and Gro-B1). Arabitol-liamocins are also observed when *A. pullulans* strain RSU 12 (NRRL 50381) is grown on Doshida medium. Similar variation is also seen for the liamocins from *A. pullulans* strains RSU 6 (NRRL 50383), RSU 29 (NRRL 50384), RSU 32 (NRRL 50382), and NBRC 108784 when grown on the four types of media (Table 6).

The results of the growth on different media (Table 6 and the MALDI-TOF MS analysis, above) demonstrate that *A. pullulans* strain CU 43 (NRRL 50380) makes only mannitol-type liamocins except when grown on Doshida's medium when it also produces ~30% arabitol-type liamocins (predominantly Ara-A1 and Ara-A2). Two *A. pullulans* strains, RSU 6 (NRRL 50383) and RSU 12 (NRRL 50381), produce more structural diversity, with arabitol-type liamocins being the major component for strain RSU 12 (NRRL 50381) on Doshida's medium and the production of glycerol-type liamocins by strains RSU 6 (NRRL 50383) on Wang and Doshida media, and RSU 12 (NRRL 50381) when cultured on Doshida's medium. Small amounts of exophilins are detected from both strains (RSU 6 (NRRL 50383) and RSU 12 (NRRL 50381)) but not triglycerides production. In addition, the RSU 12 (NRRL 50381) cultures are highly colored with an MEK-extractable red pigment ([M+Na]$^+$ ion at 476 Da.

Example 9 Stereochemistry of the Polyol Head Group

The stereochemistry of the polyol head groups on the liamocins is tested by separation on a chiral GC column. Liamocins isolated from *A. pullulans* strain RSU 12 (NRRL 50381) grown on Doshida medium are acid hydrolyzed to release the polyol head groups. The polyol head groups are converted to trifluoroacetate derivatives, and are separated on a Supelco Beta-Dex-120 chiral GC column (Sigma-Aldrich, St. Louis, Mo.). The instrument is an Agilent 6890N GC connected to an Agilent MSD 5973 mass spectrometer (Santa Clara, Calif.) running in electron impact (EI) mode, using the method described in Larsson, et al., *J. Clinical Microbiology* 32:1855-1859 (1994). Retention times for D-arabitol is 10.1 minutes; for L-arabitol, 10.4 minutes, as determined by controls of D- and L-arabitol standards. Surprisingly and unexpectedly, the arabitol head group of the Ara-type liamocins is D-arabitol, not L-arabitol. This result is surprising and unexpected because the most common stereo-isomer of arabinose is L-(−). A reduction of L-arabinose during the biosynthesis of the liamocins would therefore be expected to give L-arabitol. Yet the less common isomer D-arabitol is actually exclusively found and thus is extremely surprising and unexpected.

Example 10 Production of Liamocins with Different Polyol Head Groups

To investigate the production of structurally diverse liamocins further, *A. pullulans* strain CU 43 (NRRL 50380) and *A. pullulans* strain RSU 12 (NRRL 50381) are cultured on a variety of sugars and polyols as single carbon sources (see Example 8 and Table 6). Strains CU 43 (NRRL 50380) and RSU 12 (NRRL 50381) are chosen because when grown on sucrose strain CU 43 (NRRL 50380) produces only mannitol-type liamocins, whereas strain RSU 12 (NRRL 50381) produces a more diverse mixture and arabitol- and mannitol-type liamocins. Liamocin is collected after culturing, extracted with methyl-ethyl-ketone, and subjected to GC/MS analysis of the polyol head group following release by acid hydrolysis per the protocol set forth in Example 8 (Table 7). It is anticipated that the conditions for production of structurally diverse liamocins would be applicable to all strains of *A. pullulans*.

Table 7 summarizes the resulting diversity of liamocins produced by *Aureobasidium pullulans* strain CU 43 (NRRL 50380) when grown on different sugars or polyols as the sole carbon source. The result of this study is surprising and unexpected, because the sugar carbon source does not affect the type of liamocin nor the head group produced. Whether grown on 5% w/v sucrose, fructose, glucose, mannose, galactose, lactose, D-arabinose, L-arabinose sugars, wheat straw, alkaline hydrogen peroxide pre-treated corn fiber, or oat spelt xylan, the liamocins produced by both *A. pullulans* strain CU 43 (NRRL 50380) and *A. pullulans* strain RSU 12 (NRRL 50381) are almost exclusively the D-mannitol-type liamocins. See Table 7 for *A. pullulans* strain CU 43 (NRRL 50380) data. However, the polyol carbon sources greatly affect the type of liamocin and the head group produced. When D-arabitol, L-arabitol, xylitol, galactitol (also called dulcitol), glucitol (also called sorbitol), D-mannitol, and glycerol are added to the media, all at 5% w/v as a sole carbon source, the profile of liamocins produced are greatly affected by the choice of polyol additive. Using GC/MS analysis (except as otherwise indicated), and as shown in Table 7, when *A. pullulans* strain CU 43 (NRRL 50380) is cultured on 5% w/v D-arabitol, it produces >98% D-arabinol-type liamocins; cultured on (i) 5% w/v D-mannitol results in 100% D-mannitol-type liamocins; (ii) 5% w/v D-glucitol results in liamocins with head groups of D-glucitol (35%) and D-mannitol (65%); (iii) 5% w/v D-galactitol results in liamocins with head groups of D-galactitol (19%), D-glucitol (8%) and D-mannitol (73%); (iv) 5% w/v D-xylitol results in liamocins with head groups of D-xylitol (45%), D-arabitol (27%), and D-mannitol (28%); and (v) 5% w/v D-glycerol results in liamocins with head groups of D-glycerol (75%), D-arabitol (8%), and D-mannitol (17%) (determined using $^1$H-NMR). See Table 7 below. Similarly, liamocins with head groups of D-glucitol, D-galactitol, D-xylitol, and D-glycerol are produced by *A. pullulans* strain RSU 12 (NRRL 50381) cultured on 5% w/v D-glucitol, 5% w/v D-galactitol, 5% w/v D-xylitol, or 5% w/v D-glycerol, respectively, (plus a variety of other head groups) as determined by GC/MS analysis (as described in Example 9). Also using GC/MS analysis, when *A. pullulans* strain RSU 12 (NRRL 50381) is cultured on 5% meso-erythritol or 5% threitol, primarily, D-mannitol-liamocins (95%) and, to a lesser amount, D/L-erythritol (5%) or threitol (5%), respectively, is produced. However, surprisingly and unexpectedly, when the carbon source is 5% L-threitol, primarily threitol liamocin (about 75%) and a smaller amount of D-mannitol-liamocin (about 25%) are produced. The polyol head groups released by acid hydrolysis are shown to be a 1.67:1 mixture of D-xylitol-liamocins:D-arabitol-liamocins from *A. pullulans* strain CU 43 (NRRL 50380) cultured on D-xylitol, and >98% D-arabitol from *A. pullulans* strain CU 43 (NRRL 50380) cultured on D-arabitol. Furthermore, the yields of liamocins are relatively unaffected by the nature of the polyol nutrient, and are typically 120-150 mg dry weight for the 100 mL cultures.

TABLE 7

| | % Polyol Headgroups Detected from the Acid-Hydrolyzed Liamocins[2] | | | | | | | | |
|---|---|---|---|---|---|---|---|---|---|
| Carbon Source[1] | Gro (3.5) | Thr (6.1) | Ery (6.7) | Rib (10.8) | Ara (11.1) | Xyl (11.4) | Man (15.2) | Glc (15.25) | Gal (15.28) |
| sucrose | — | — | — | — | — | — | 100 | — | — |
| lactose | — | — | — | — | — | — | 100 | — | — |
| D-fructose[3] | — | — | — | — | — | — | 100 | — | — |
| D-glucose[3] | — | — | — | — | — | — | 100 | — | — |
| D-mannose[3] | — | — | — | — | — | — | 100 | — | — |
| D-galactose[3] | — | — | — | — | — | — | 100 | — | — |
| D-arabinose[4] | — | — | — | — | — | — | 100 | — | — |
| L-arabinose[4] | — | — | — | — | — | — | 100 | — | — |
| D-xylose[4] | — | — | — | — | — | — | 100 | — | — |
| D-mannitol[5] | — | — | — | — | — | — | 100 | — | — |
| D-glucitol[5] | — | — | — | — | — | — | 65 | 35 | — |
| D-galactitol[5] | — | — | — | — | — | — | 73 | 8 | 19 |
| D-arabitol[6] | — | — | — | — | >98 | — | <2 | — | — |
| L-arabitol[6] | — | — | — | — | 62 | — | 38 | — | — |
| D-xylitol[6] | — | — | — | — | 27 | 45 | 28 | — | — |
| D-ribitol[6] | — | — | — | 18 | 63 | — | 19 | — | — |
| L-threitol[7] | — | ~75 | — | — | — | — | ~25 | — | — |
| D-threitol | — | 5 | — | — | — | — | 95 | — | — |

TABLE 7-continued

| Carbon Source[1] | % Polyol Headgroups Detected from the Acid-Hydrolyzed Liamocins[2] | | | | | | | | |
|---|---|---|---|---|---|---|---|---|---|
| | Gro (3.5) | Thr (6.1) | Ery (6.7) | Rib (10.8) | Ara (11.1) | Xyl (11.4) | Man (15.2) | Glc (15.25) | Gal (15.28) |
| Meso-erythritol[7] | — | — | 5 | — | — | — | 95 | — | — |
| D-glycerol[8] | 75 | — | — | — | 8 | — | 17 | — | — |

[1]Sole carbon source at 5% in PM medium (above the center blank-line the carbon sources are sugars, and below the line they are polyols).
[2]Analysis by GC/MS of the polyols head groups from acid hydrolyzed liamocins from *A. pullulans* CU 43 (NRRL 50380). Retention times in parenthesis.
[3]6-carbon hexose sugars;
[4]5-carbon pentose sugars;
[5]6-carbon polyols;
[6]5-carbon polyols;
[7]4-carbon polyol;
[8]3-carbon polyol.

Example 11 Antibacterial Activity of D-Xylitol:D-Arabitol Liamocins Mixtures, Pure D-Arabitol Liamocins, and D-Mannitol-Liamocins are Compared To produce liamocins with alternative (non-mannitol) head groups, *A. pullulans* strain CU 43 (NRRL 50380) is cultured on 5% w/v xylitol to produce a 1.67:1 mixture of xylitol-liamocins:arabitol-liamocins and on 5% w/v D-arabitol to produce >98% D-arabitol-liamocins, as described in Example 10 above. Further, *A. pullulans* strain CU 43 (NRRL 50380) is also cultured on 5% w/v mannitol to produce 100% D-mannitol-liamocins. The liamocins are isolated from each cultures by extraction with 2-butanone, as described previously. Each set of extracted liamocins (1.67:1 mixture of xylitol:arabitol; >98%% D-arabitol; and 100% D-mannitol) are tested for antibacterial activity by measuring the minimum inhibitory concentration (MIC) against *S. agalactiae* NRRL B-1815 according to the broth microdilution method described in Example 1 above. *S. agalactiae* is susceptible to antibacterial activity of the liamocins with alternative head groups. MICs for liamocins with either >98%% D-arabitol or with a mixture of D-xylitol:D-arabitol (1.67:1) head groups are higher than the 100% D-mannitol liamocins. See Table 8 below. This activity suggests that the antibacterial activity of the non-mannitol liamocins is weaker than the mannitol liamocins, but D-arabitol liamocin still has good activity against *Streptococcus* spp. Yet, after D-arabitol liamocins are separated by HPLC (as described above) into D-arabitol liamocin liamocin trimers (Formulas 2 and 3 where $R_4$ and $R_5$ are Formula 14) and D-arabitol liamocin tetramers (Formulas 4 and 5 where $R_6$ and $R_7$ are Formula 14); and the MIC against *S. agalactiae* for the trimers and tetramers are assessed, the D-arabitol liamocin tetramers demonstrate better killing activity than the trimers.

TABLE 8

| Growth substrate | Liamocins head group | MIC (µg/ml) |
|---|---|---|
| D-mannitol | D-mannitol | 16 |
| D-arabitol | D-arabitol | 64 |
| Xylitol | D-xylitol:D-arabitol (1.67:1) | 128 |

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation. All documents cited herein are incorporated by reference. Recitation of ranges of values herein are merely intended to serve as a shorthand method of referring individually to each separate value falling within the range, unless otherwise indicated herein, and each separate value is incorporated into the specification as if it is individually recited herein. For example, if the range 10-15 is disclosed, then 11, 12, 13, and 14 are also disclosed. When the term "about" or "approximately" is used, the indicated numeric value includes a 10% increase and a 10% decrease of that value. So, "approximately ten" includes all numbers between "nine" and "eleven"; "about one hundred" includes all numbers between "ninety" and "one-hundred ten". As used in the specification and claims, the singular form "a", "an" and "the" include plural references unless the context clearly dictates otherwise.

The invention claimed is:

1. A method of preventing a disease caused by *S. agalactiae, S. infantarius, S. mitis, S. mutans, S. pneumonia, S. salivarius, S. suis,* or *S. uberis* in an animal susceptible to said disease comprising administering an effective amount of a composition to prevent the growth of said *S. agalactiae, S. infantarius, S. mitis, S. mutans, S. pneumonia, S. salivarius, S. suis,* or *S. uberis* in or on said animal, wherein said composition comprises one or more of the compounds of Formula 1, optionally a carrier, and optionally a diluent; and wherein said Formula 1 is Formula 1

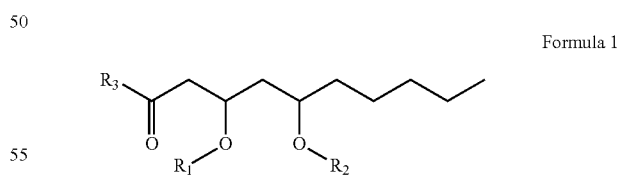

where $R_1$ is, independently, either $COCH_3$ or H; and $R_2$ is, independently, between two to ten O-linked 3,5-dihydroxydecanoate; and $R_3$ is, independently, one of the following: L- or D-glycerol, L- or D-threitol, L- or D-erythritol, L- or D-arabitol, L- or D-xylitol, L- or D-lyxitol, L- or D-ribitol, L- or D-allitol, L- or D-altritol, L- or D-mannitol, L- or D-iditol, L- or D-gulitol, L- or D-glucitol, L- or D-galactitol, L- or D-talitol, 2-amino-D-mannitol, 2N-acetylamino-D-mannitol, L-rhamnitol, or D-fucitol; and a combination thereof.

2. The method of claim 1, wherein said compound of Formula 1 is selected from the group comprising L-mannitol liamocin A1, L-mannitol liamocin A2, L-mannitol liamocin B1, L-mannitol liamocin B2, D-mannitol liamocin A1, D-mannitol liamocin A2, D-mannitol liamocin B1, D-mannitol liamocin B2, L-arabitol liamocin A1, L-arabitol liamocin A2, L-arabitol liamocin B1, L-arabitol liamocin B2, D-arabitol liamocin A1, D-arabitol liamocin A2, D-arabitol liamocin B1, D-arabitol liamocin B2, L-threitol liamocin A1, L-threitol liamocin A2, L-threitol liamocin B1, L-threitol liamocin B2, D-threitol liamocin A1, D-threitol liamocin A2, D-threitol liamocin B1, D-threitol liamocin B2, L-glycerol liamocin A1, L-glycerol liamocin A2, L-glycerol liamocin B1, L-glycerol liamocin B2, D-glycerol liamocin A1, D-glycerol liamocin A2, D-glycerol liamocin B1, and D-glycerol liamocin B2.

3. The method of claim 1, wherein said administering said composition occurs via topical administration, oral administration, or parenteral administration to said animal.

4. The method of claim 1, wherein said animal is selected from the group consisting of a mammal, a bird, a fish, an amphibian, and a reptile.

\* \* \* \* \*